(12) United States Patent
Bazin-Lee et al.

(10) Patent No.: US 10,774,099 B2
(45) Date of Patent: Sep. 15, 2020

(54) PHOSPHOLIPIDATION OF IMIDAZOQUINOLINES AND OXOADENINES

(71) Applicant: GLAXOSMITHKLINE BIOLOGICALS, SA, Rixensart (BE)

(72) Inventors: Helene G. Bazin-Lee, Hamilton, MT (US); Laura S. Bess, Hamilton, MT (US); David A. Johnson, Hamilton, NC (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/060,142

(22) PCT Filed: Dec. 12, 2016

(86) PCT No.: PCT/EP2016/080647
§ 371 (c)(1),
(2) Date: Jun. 7, 2018

(87) PCT Pub. No.: WO2017/102654
PCT Pub. Date: Jun. 22, 2017

(65) Prior Publication Data
US 2018/0273560 A1 Sep. 27, 2018

Related U.S. Application Data

(60) Provisional application No. 62/266,858, filed on Dec. 14, 2015.

(51) Int. Cl.
*C07F 9/10* (2006.01)
*C07F 9/6558* (2006.01)
*C07F 9/6561* (2006.01)

(52) U.S. Cl.
CPC ............ *C07F 9/65583* (2013.01); *C07F 9/10* (2013.01); *C07F 9/65616* (2013.01)

(58) Field of Classification Search
CPC ... C07F 9/65583; C07F 9/10; C07F 9/656161
USPC .......................................................... 546/82
See application file for complete search history.

(56) References Cited

U.S. PATENT DOCUMENTS

| 8,624,029 | B2 * | 1/2014 | Johnson | ............... | C07D 471/06 546/23 |
| 8,946,421 | B2 * | 2/2015 | Johnson | ............... | C07D 471/06 546/82 |
| 2018/0362560 | A1 * | 12/2018 | Bazin-Lee | ............ | C07F 9/6561 |

FOREIGN PATENT DOCUMENTS

| WO | WO-2010048520 A1 * | 4/2010 | ........... C07D 471/04 |
| WO | 2011/017611 A1 | 2/2011 | |
| WO | 2017/102652 A1 | 6/2017 | |

OTHER PUBLICATIONS

Smith et al., Evaluation of novel synthetic TLR7/8 agonists as vaccine adjuvants, Vaccine 34, pp. 4304-4312.
Bazin et al., Phospholipidation of TLR7/8-active imidazoquinolines using a tandem phosphoramidite method, Tetrahedron Letters 57, 2016, pp. 2063-2066.

* cited by examiner

*Primary Examiner* — Rita J Desai
(74) *Attorney, Agent, or Firm* — Birch, Stewart, Kolasch & Birch, LLP

(57) ABSTRACT

The present invention relates to a process for phospholipidation of imidazoquinolines and oxoadenines. More particularly, the present invention relates to a high-yielding and scalable procedure for the phospholipidation of imidazoquinolines and oxoadenines which obviates the need to isolate unstable phosphoramidite intermediates. This process may be used for the phospholipidation of toll-like receptor 7 (TLR7)—active and toll-like receptor (TLR8)—active imidazoquinolines and oxoadenines.

11 Claims, No Drawings

PHOSPHOLIPIDATION OF IMIDAZOQUINOLINES AND OXOADENINES

STATEMENT REGARDING FEDERALLY SPONSORED RESEARCH

This invention was made with Government support under contract # HHSN272200900036C awarded by the National Institutes of Health. The Government has certain rights in the invention.

BACKGROUND OF THE INVENTION

The present invention relates to a process for phospholipidation of imidazoquinolines and oxoadenines. More particularly, the present invention relates to a high-yielding and scalable procedure for the phospholipidation of imidazoquinolines and oxoadenines which obviates the need to isolate unstable phosphoramidite intermediates. This process may be used for the phospholipidation of toll-like receptor 7 (TLR7)—active and toll-like receptor 8 (TLR8)—active imidazoquinolines and oxoadenines.

Toll-like receptors (TLRs) are a family of more than 10 structurally related receptors on innate immune cells that detect pathogen-specific components common to large classes of microbial invaders. Activation of these receptors leads to the expression of inflammatory cytokines/chemokines and type I interferons alpha and beta (IFNα/β) important for effective innate and adaptive immune responses to infectious disease and cancer.

In the case of TLR7 and TLR8 activation, a few different classes of small-molecule mimetics of the natural uridine- and/or guanosine-rich viral ssRNA ligands have been identified (Heil et al. *Eur. J. Immunol.* 2003, 33, 2987-2997, Hemmi et al. *Nat. Immunol.* 2002, 3, 196-200, Lee et al. *Proc. Natl. Acad. Sci. U.S.A.* 2006, 103, 1828-1833), including oxoadenine analogs (Hirota et al. *J. Med. Chem.* 2002, 45, 5419; WO 2007/034882 PCT/JP2006/318758, Dainippon Sumitomo Pharma Co. Ltd./AstraZeneca Aktiebolag) and 1H-imidazo[4,5-c]quinolines (Gerster et al. *J. Med. Chem.* 2005, 48, 3481-3491) such as imiquimod, which is approved for topical treatment of certain skin diseases and known to primarily activate TLR7, and the structurally related imidazoquinoline resiquimod, which potently activates both TLR7 and TLR8 (Miller et al. *Drug News Perspect.* 2008, 21, 69-87).

Since TLR7 and TLR8 are broadly expressed in dendritic cells (DCs) and other antigen presenting cells, TLR7/8 agonists and their derivatives may be especially useful as vaccine adjuvants. However, oral and topical preparations of imiquimod and resiquimod and other small-molecule TLR7/8 agonists can exhibit serious side effects, and clinical trials with certain TLR7/8 agonists have been suspended over safety concerns (Horscroft et al. *J. Antimicrob. Chemother.* 2012, 67, 789-801, Strominger, N. L.; Brady, R.; Gullikson, G.; Carpenter, D. O. *Brain Res. Bull.* 2001, 55, 445-451). In addition, since TLR7 and TLR8 are located in endosomal/lysosomal compartments (Lee et al. *Proc. Natl. Acad. Sci. U.S.A.* 2003, 100, 6646-6651), cellular uptake is prerequisite for cellular activation by TLR7/8 ligands. Thus, there is considerable interest in strategies that will increase the penetration of the TLR7/8 ligand into DCs and other immune cells as well as ameliorate toxic effects. Lipid conjugation of nucleoside drugs including TLR7/8 agonists (Chan et al. *Bioconjugate Chem.* 2009, 20, 1194-1200) is one strategy known to facilitate endocytosis, enhance oral bioavailability, and decrease toxic side effects. Such nucleolipids can also be incorporated into liposomes and other biodegradable nanoparticles to help protect the drug from degradation and further reduce toxicity through a depot effect (Rosemeyer, H. *Chemistry & Biodiversity* 2005, 2, 977-1063).

SUMMARY OF THE INVENTION

The present invention relates to a process for preparing compounds of formula (I) and formula (II) that comprises an imidazoquinoline or an oxoadenine molecule covalently linked to a phospho group.

Formula (I)

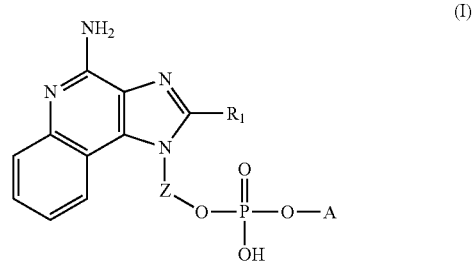

wherein $R_1$ is selected from H, $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino and $C_{1-6}$alkoxy$C_{1-6}$alkoxy; wherein the $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino or $C_{1-6}$alkoxy$C_{1-6}$alkoxy is branched or unbranched and optionally terminally substituted with a hydroxyl, amino, thio, hydrazino, hydrazido, azido, acetylenyl, carboxyl, or maleimido group;

Z is selected from $C_2$-$C_6$ alkyl and $C_2$-$C_6$ alkenyl, wherein the $C_2$-$C_6$ alkyl or $C_2$-$C_6$ alkenyl is unsubstituted or terminally substituted by —(O—$C_2$-$C_6$alkyl)$_{1-6}$—;

A is

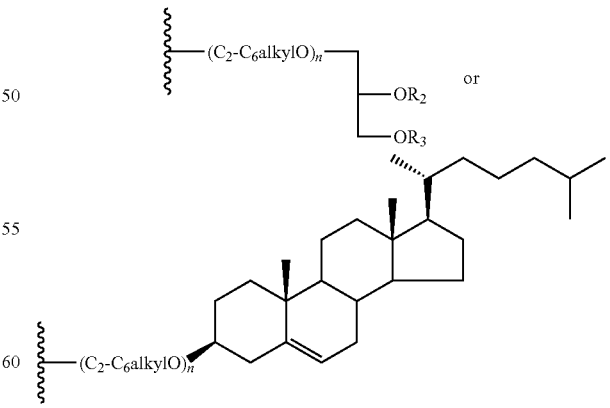

wherein $R_2$ is H or a straight or branched, optionally unsaturated, $C_4$-$C_{24}$ alkyl, or a straight or branched, optionally unsaturated, $C_4$-$C_{24}$, acyl;

$R_3$ is a straight or branched, optionally unsaturated, $C_4$-$C_{24}$ alkyl or a straight or branched, optionally unsaturated, $C_4$-$C_{24}$ acyl;

n is 0, 1, 2, 3, 4, 5, 6, 7, 8, 9, 10, 11, 12, 13, 14, 15, 16, 17, 18, 19, or 20.

Formula II:

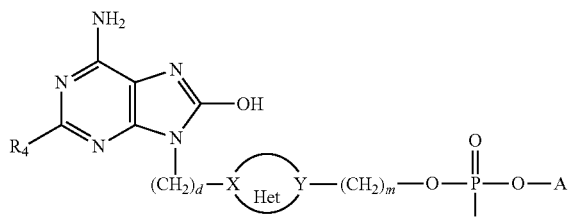

(II)

wherein $R_4$ is selected from $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino and $C_{1-6}$alkoxy$C_{1-6}$alkoxy; wherein the $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino or $C_{1-6}$alkoxy$C_{1-6}$alkoxy is branched or unbranched and optionally terminally substituted with a hydroxyl, amino, thio, hydrazino, hydrazido, azido, acetylenyl, carboxyl, or maleimido group;

d is 0, 1, 2, 3, 4, 5 or 6;

Het is a four-, five-, or six membered saturated nitrogen heterocycle wherein

X,Y=CH or N, and at least one of X and Y is a nitrogen atom;

m is 0, 1, 2, 3, 4, 5 or 6;

A is

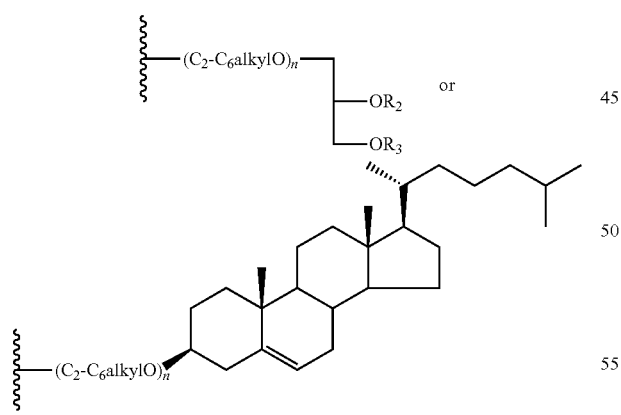

wherein $R_2$ is H or a straight or branched, optionally unsaturated, $C_4$-$C_{24}$ alkyl, or a straight or branched, optionally unsaturated, $C_4$-$C_{24}$ acyl;

$R_3$ is a straight or branched, optionally unsaturated, $C_4$-$C_{24}$ alkyl or a straight or branched, optionally unsaturated, $C_4$-$C_{24}$ acyl;

n is 0, 1, 2, 3, 4, 5, 6, 7, 8, 9, 10, 11, 12, 13, 14, 15, 16, 17, 18, 19, or 20.

As a first aspect, the present invention provides a process for preparing compounds of formula (I). The process comprises the steps of:

a) reacting a compound of formula (III)

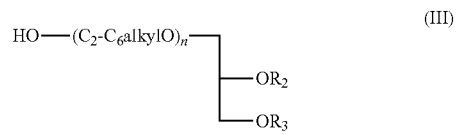

(III)

with a compound of formula (V)

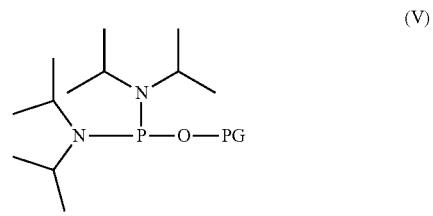

(V)

wherein

PG is a protecting group suitable for hydroxyl protection, including but not limited to cyanoethyl, methyl, ethyl, benzyl and allyl group;

all other variables are as defined above for formula (I);

to prepare a compound of formula (VI)

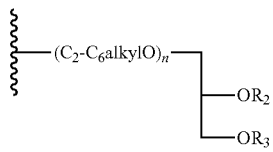

(VI)

wherein

R is

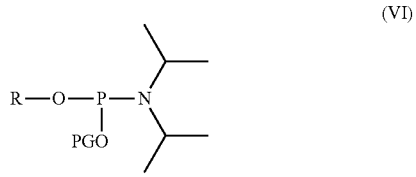

all other variables are as defined above for formula (I);

b) reacting a compound of formula (VI) with a compound of formula (VII)

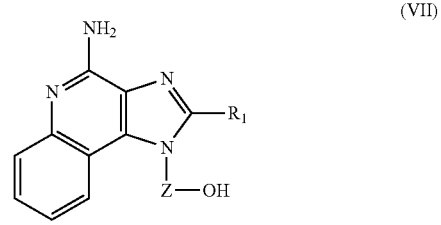

(VII)

to prepare a compound of formula (IX)

$$R-O-P-O-R' \atop OPG \qquad (IX)$$

wherein
R is $$\{-(C_2\text{-}C_6\text{alkylO})_n-\begin{array}{c}-OR_2\\-OR_3\end{array}$$

R' is

[structure: 4-amino-imidazoquinoline with $R_1$ substituent and Z linker]

and all other variables are as defined above for formula (I);

c) oxidizing a compound of formula (IX) and removing the hydroxyl protecting group to obtain a compound of formula (I).

In another aspect, the present invention provides another process for preparing a compound of formula (I). This process comprises the steps of:

a) reacting a compound of formula (IV)

(IV)

[structure: cholesterol with HO-(C$_2$-C$_6$alkylO)$_n$ substituent]

with a compound of formula (V)

(V)

[structure: bis(diisopropylamino)phosphine-O-PG]

wherein
PG is a protecting group suitable for hydroxyl protection, including but not limited to cyanoethyl, methyl, ethyl, benzyl and allyl group; and all other variables are as defined above for formula (I); to prepare a compound of formula (VI)";

$$R''-O-P-N(iPr)_2 \atop PGO \qquad (VI)''$$

wherein
R" is

[cholesteryl-(C$_2$-C$_6$alkylO)$_n$- structure]

all other variables are as defined above for formula (I);

b) reacting a compound of formula (VI)" with a compound of formula (VII)

(VII)

[structure: 4-amino-imidazoquinoline with $R_1$ and Z-OH]

to prepare a compound of formula (IX)";

$$R''-O-P-O-R' \atop OPG \qquad (IX)''$$

wherein
R" is

[cholesteryl-(C$_2$-C$_6$alkylO)$_n$- structure]

R' is

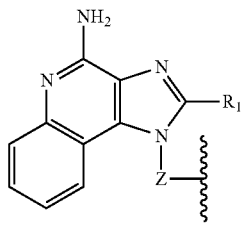

all other variables are as defined above for formula (I);
c) oxidizing a compound of formula (IX)" and removing the hydroxyl protecting group to obtain a compound of formula (I).

In a third aspect, the present invention provides a process for preparing compounds of formula (II). The process comprises the steps of:
a) reacting a compound of formula (III)

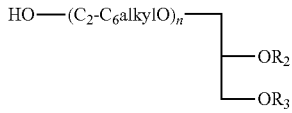
(III)

with a compound of formula (V)

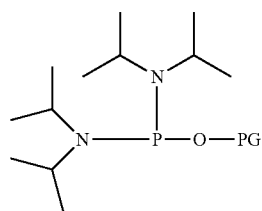
(V)

wherein
PG is a protecting group suitable for hydroxyl protection, including but not limited to cyanoethyl, methyl, ethyl, benzyl and allyl group;
all other variables are as defined above for formula (II);

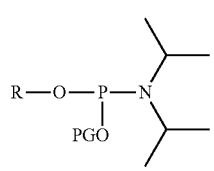
(VI)

to prepare a compound of formula (VI) (VI)
wherein
R is

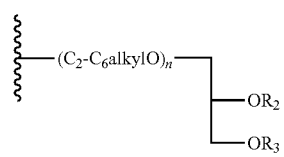

all other variables are as defined above for formula (II);
b) reacting a compound of formula (VI) with a compound of formula (VIII)

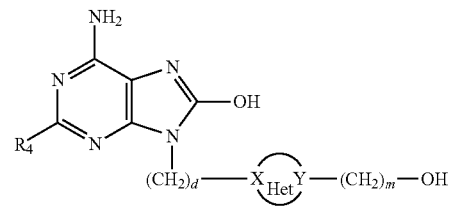
(VIII)

to prepare a compound of formula (IX)*

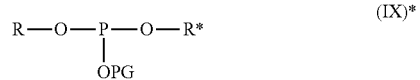
(IX)* wherein
R is

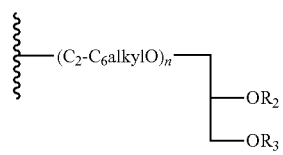

R* is

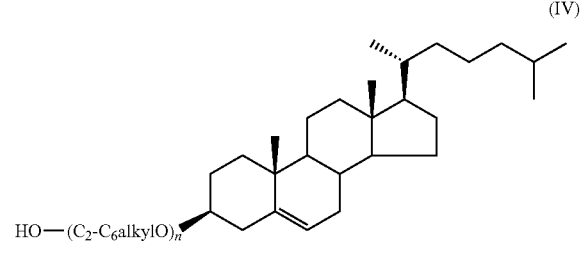

all other variables are as defined above for formula (II);
c) oxidizing a compound of formula (IX)* and removing the hydroxyl protecting group to obtain a compound of formula (II).

In a forth aspect, the present invention provides another process for preparing a compound of formula (II). This process comprises the steps of:
a) reacting a compound of formula (IV)

(IV)

HO—$(C_2\text{-}C_6\text{alkylO})_n$ with a compound of formula (V)

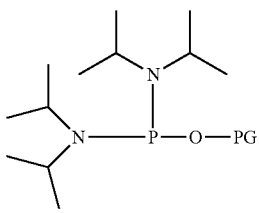
(V)

wherein
PG is a protecting group suitable for hydroxyl protection, including but not limited to cyanoethyl, methyl, ethyl, benzyl and allyl group;
all other variables are as defined above for formula (II);
to prepare a compound of formula (VI)'';

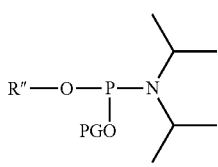
(VI)'' wherein
R'' is

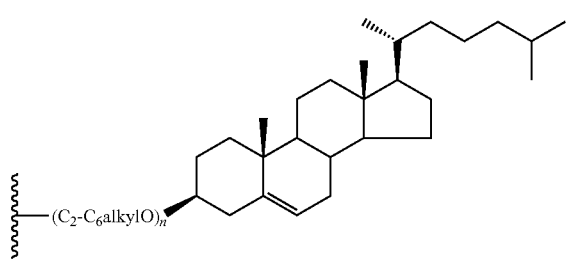

all other variables are as defined above for formula (II);
b) reacting a compound of formula (VI)'' with a compound of formula (VIII)

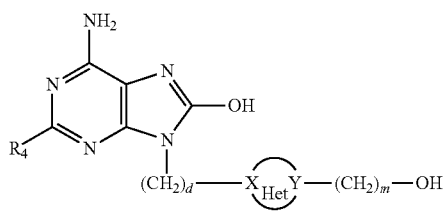
(VIII)

to prepare a compound of formula (IX)*'';

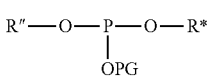
(IX)*'' wherein
R'' is

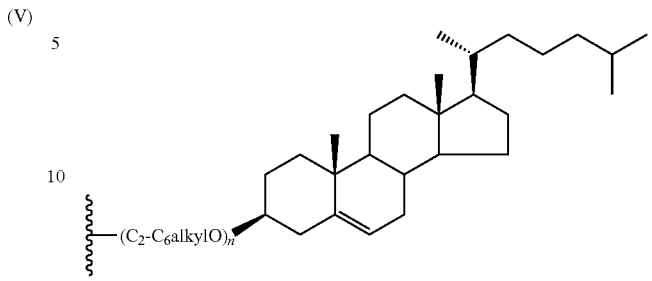

R* is

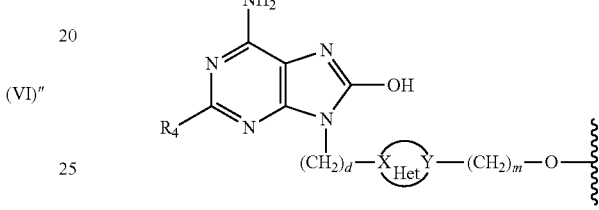

all other variables are as defined above for formula (II);
c) oxidizing a compound of formula (IX)*'' and removing the hydroxyl protecting group to obtain a compound of formula (II).

Further aspects of the present invention are described in the description of particular embodiments, examples, and claims which follow.

DETAILED DESCRIPTION OF THE PREFERRED EMBODIMENTS

As used herein, "a compound of formula (I)" means a compound of formula (I) or a pharmaceutically acceptable salt or solvate thereof. "A compound of formula (II)" means a compound of formula (II) or a pharmaceutically acceptable salt or solvate thereof.

As used herein, "a compound of the invention" means a compound of formula (I) or formula (II) or a pharmaceutically acceptable salt or solvate thereof.

As used herein, the term "optionally" means that the subsequently described event(s) may or may not occur, and includes both event(s) that occur and events that do not occur.

Certain compounds of formula (I) or formula (II) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) or formula (II) as mixtures with isomers thereof in which one or more chiral centers are inverted.

Certain compounds of the invention may exist in tautomeric forms. It will be understood that the present invention encompasses all of the tautomers of the compounds of the invention whether as individual tautomers or as mixtures thereof whether or not explicitly indicated in the present formulas.

Suitable pharmaceutically acceptable salts according to the present invention will be readily determined by one skilled in the art and will include, for example, salts prepared from inorganic bases such as lithium hydroxide, sodium hydroxide, potassium hydroxide, lithium carbonate, lithium hydrogen carbonate, sodium carbonate, sodium hydrogen carbonate, potassium carbonate, potassium hydrogen carbonate, as well as potassium tert-butoxide and organic bases such as diethyl amine, lysine, arginine, choline hydroxide, choline bicarbonate, tris (hydroxymethyl) aminomethane (tromethamine), triethanolamine, diethanolamine, and ethanolamine.

When used in medicine, the salts of a compound of formula (I) or formula (II) should be pharmaceutically acceptable, but pharmaceutically unacceptable salts may conveniently be used to prepare the corresponding free base or pharmaceutically acceptable salts thereof.

As used herein, the term "solvate" refers to a crystal form containing the compound of formula (I) or formula (II) or a pharmaceutically acceptable salt thereof and either a stoichiometric or a non-stoichiometric amount of a solvent. Solvents, by way of example, include water (thus producing hydrates), methanol, ethanol, or acetic acid. Hereinafter, reference to a compound of formula (I) or formula (II) is to any physical form of that compound, unless a particular form, salt or solvate thereof is specified.

Processes for preparing pharmaceutically acceptable salts of the compounds of formula (I) or formula (II) are conventional in the art. See, e.g., Burger's Medicinal Chemistry And Drug Discovery 5th Edition, Vol 1: Principles And Practice.

The compounds of the invention of formula (I) or formula (II) may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

It will be appreciated from the foregoing that included within the scope of the invention are solvates, isomers and polymorphic forms of the compounds of formula (I) and formula (II) and salts thereof.

A compound of formula (I) or formula (II) may be prepared using the processes depicted below.

Scheme 1

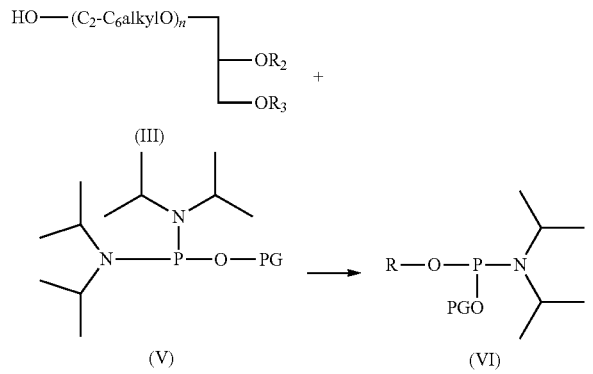

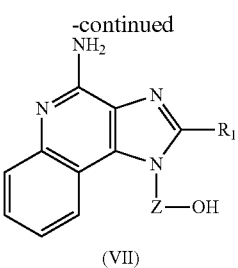

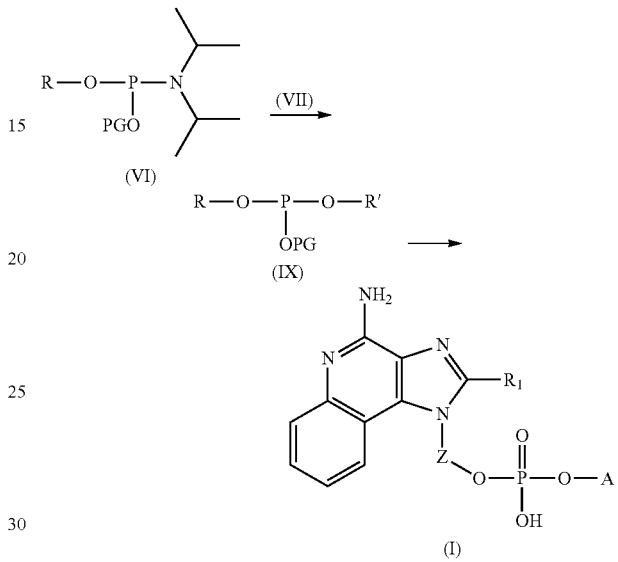

wherein

PG is a protecting group suitable for hydroxyl protection, including but not limited to cyanoethyl, methyl, ethyl, benzyl and allyl group;

R is

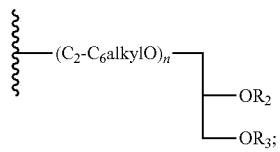

R' is

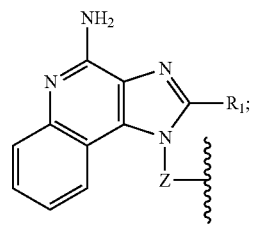

all other variables are as defined above for formula (I).

In general, the process for preparing a compound of formula (I) as depicted in Scheme 1 comprises the steps of:

a) reacting a compound of formula (III) with a compound of formula (V) to prepare a compound of formula (VI);

b) reacting a compound of formula (VI) with a compound of formula (VII) to to prepare a compound of formula (IX); and c) oxidizing a compound of formula (IX) and removing the hydroxyl protecting group to obtain a compound of formula (I).

R" is

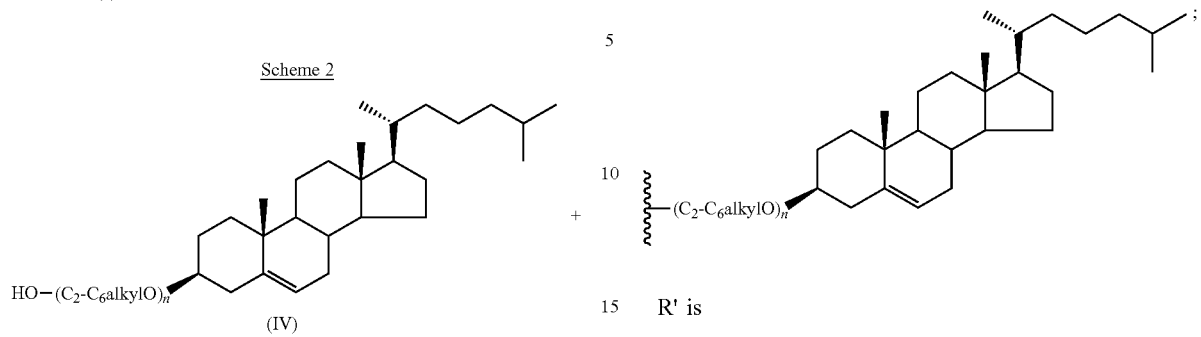

R' is and
all other variables are as defined above for formula (I);

In general, the process for preparing a compound of formula (I) as depicted in Scheme 2 comprises the steps of:

a) reacting a compound of formula (IV) with a compound of formula (V) to prepare a compound of formula (VI)";

b) reacting a compound of formula (VI)" with a compound of formula (VII) to prepare a compound of formula (IX)"; and c) oxidizing a compound of formula (IX)" and removing the hydroxyl protecting group to obtain a compound of formula (I).

wherein

PG is a protecting group suitable for hydroxyl protection, including but not limited to cyanoethyl, methyl, ethyl, benzyl and allyl group;

-continued

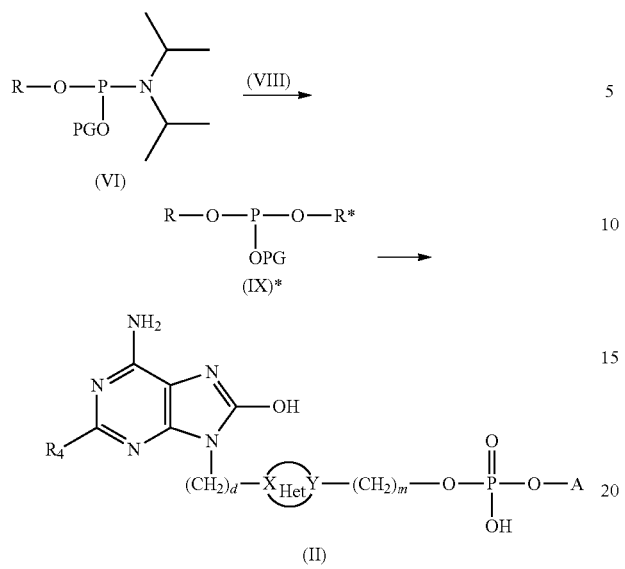

wherein
PG is a protecting group suitable for hydroxyl protection, including but not limited to cyanoethyl, methyl, ethyl, benzyl and allyl group;
R is

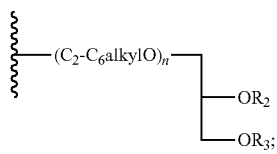

R* is

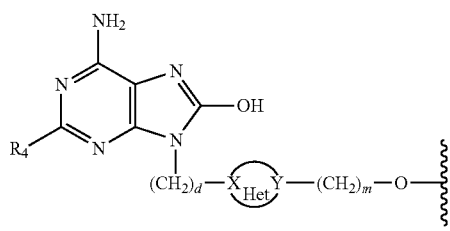

all other variables are as defined above for formula (II).

In general, the process for preparing a compound of formula (II) as depicted in Scheme 3 comprises the steps of:

a) reacting a compound of formula (III) with a compound of formula (V) to prepare a compound of formula (VI); and b) reacting a compound of formula (VI) with a compound of formula (VIII) to prepare a compound of formula (IX)*; and c) oxidizing a compound of formula (IX)* and removing the hydroxyl protecting group to obtain a compound of formula (II).

Scheme 4

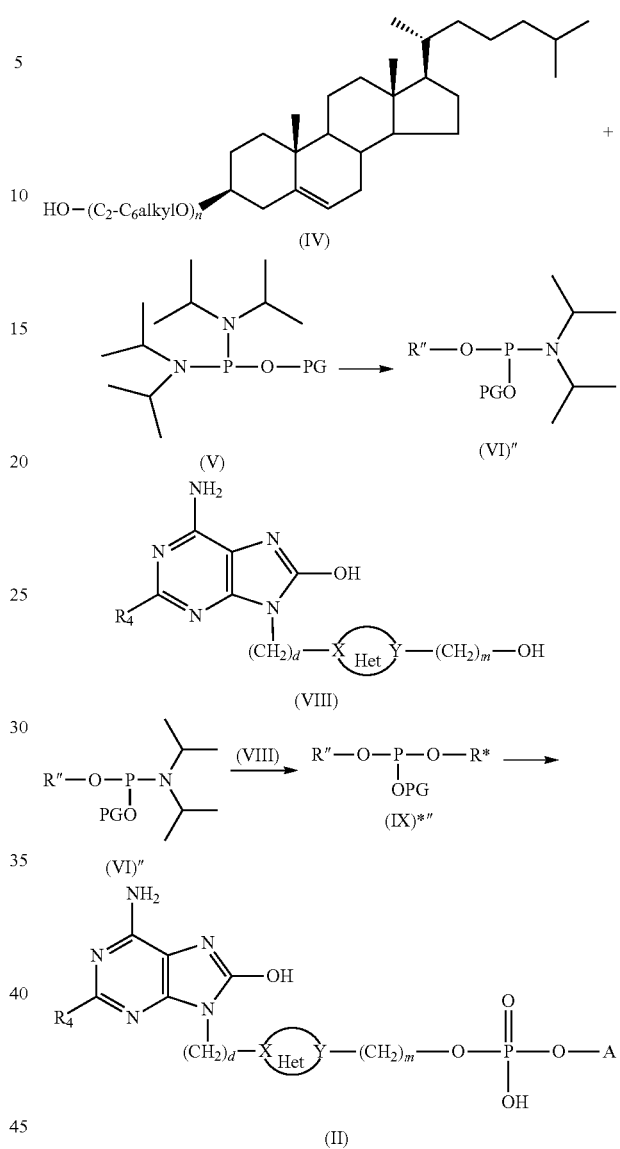

wherein
PG is a protecting group suitable for hydroxyl protection, including but not limited to cyanoethyl, methyl, ethyl, benzyl and allyl group;
R" is

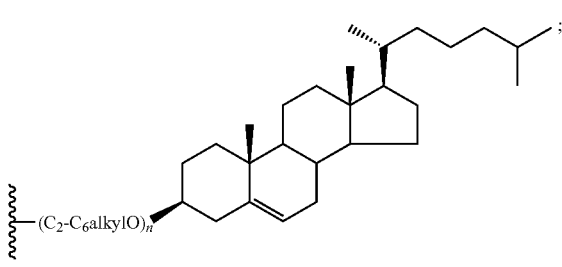

R* is

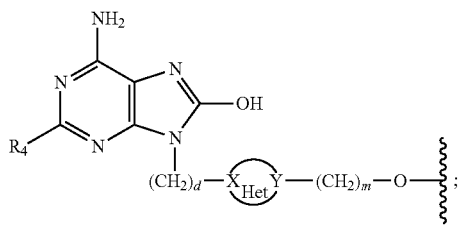

all other variables are as defined above for formula (II).

In general, the process for preparing a compound of formula (II) as depicted in Scheme 4 comprises the steps of:

a) reacting a compound of formula (IV) with a compound of formula (V) to prepare a compound of formula (VI)'';

b) reacting a compound of formula (VI)'' with a compound of formula (VIII) to prepare a compound of formula (IX)*''';

c) oxidizing a compound of formula (IX)*''' and removing the hydroxyl protecting group to obtain a compound of formula (II).

More particularly, the compound of formula (VI) or (VI)'' may be prepared by reacting the compound of formula (III) or (IV) with a of formula (V) in the presence of a suitable phosphoramidite coupling reagent such as 1H-tetrazole, substituted terazole, dicyanoimidazole, imidazolium triflate or any such coupling reagents known to those skilled in the art, in an aprotic solvent such as but not limited to methylene chloride, between 0° C. and ambient temperature.

The compound of formula (VI) or (VI)'', which may be purified by chromatography on silica gel but is preferably not isolated or purified, may be directly reacted upon formation with compound of formula (VII) or (VIII) in the presence of a suitable phosphoramidite coupling reagent such as 1H-tetrazole, substituted tetrazole, dicyanoimidazole, imidazolium triflate or any such coupling reagents known to those skilled in the art, in an aprotic solvent such as but not limited to methylene chloride, between 0° C. and ambient temperature to prepare compounds of formula (IX), (IX)'', (IX)* and (IX)*'''.

The compound of formula (IX), (IX)'', (IX)* or (IX)*''' is converted to a compound of formula (I) or formula (II) by oxidation using phosphorus oxidizing agent such as but not limited to m-chloroperbenzoic acid, hydrogen peroxide, iodine/pyridine/water, or tert-butylperoxide followed by removal of the protecting group using techniques known to those skilled in the art.

In one embodiment, compounds of formula (I) or formula (II) are prepared by:

(i) adding 1H-tetrazole (2.1 eq) in several portions to a methylene chloride solution of a compound of formula (III) or formula (IV) (2.0 eq) followed by the phosphordiamidite reagent of formula (V) (2.1 eq) and reacting 30 min to 1 h at room temperature after the last addition of tetrazole, (ii) cooling the reaction mixture to 0° C., (iii) adding a compound of formula (VII) or (VIII) (1.0 eq) and imidazolium triflate (1.5 eq), and reacting at 0° C. for up to 30 min then at room temperature for 1 hour to 24 hours, and (iv) subsequent oxidation of a compound of formula (IX), (IX)'', (IX)* or (IX)*''' (purified or not) with tert-butyl peroxide (1.5 eq) followed by protecting group deprotection.

In one embodiment, 1H-tetrazole is added to a compound of formula (III) or formula (IV) in ~30 min (for example, 4 portions; for example, one added every ten minutes). As used in this embodiment, ~30 min means + or −10 minutes, 20-40 minutes.

In another embodiment, a compound of formula (V) is added and reacted with a compound of formula (III) or a compound of formula (IV), forming a compound of formula (VI) or (VI)'', to which a compound of formula (VII) or formula (VIII) is added before the addition of imidazolium triflate.

In another embodiment, the reaction mixture containing the compound of formula (VI) or (VI)'' is cooled to 0° C. before the addition of a compound of formula (VII) or formula (VIII).

In one embodiment, the protecting group is cyanoethyl.

In another embodiment, deprotection is performed with triethylamine (TEA).

In a preferred embodiment, the protecting group is cyanoethyl and deprotection is with triethylamine (TEA).

In one embodiment, the coupling agent used with a compound of formula (III) or formula (IV) and a compound of formula (V) is at 2.1 equivalents, the compound of formula (III) or formula (IV) is at 2.0 equivalents, the compound of formula (V) is at 2.1 equivalents, the compound of formula (VII) or formula (VIII) is at 1.0 equivalent and the oxidizing agent for the compound of formula (IX), (IX)'', (IX)* or (IX)*''' is at 1.5 equivalent.

In one embodiment, imidazolium triflate is added with the compound of formula (VII) or the compound of formula (VIII) to the same reaction mixture produced by the reaction of compound of formula (V) with the compound of formula (III) or the compound of formula (IV).

The following examples are intended for illustration only and are not intended to limit the scope of the invention in any way, the present invention being defined by the claims.

In the examples, the following terms have the designated meaning:

eq=equivalents;
ES TOF-MS=electrospray time of flight mass spectroscopy;
h=hour;
H=hydrogen atom;
Hz=Hertz; MHz=megaHertz;
min=minute;
M=molar;
NMR=nuclear magnetic resonance;
rt=room temperature;
TEA=triethylamine;
v=volume.

Example 1: General Procedure for the Synthesis of Phosphotriester IX

To a solution of III or IV (2.0 eq) in anhydrous methylene chloride (0.4 M) was added 2-cyanoethyl N,N,N',N'-tetraisopropylphosphordiamidite V (2.1 eq) at rt. 1H-tetrazole (2.1 eq) was then added in four portions over 20 minutes and the reaction mixture stirred at rt for 1 h. After 1 h, the resulting phosphoramidite VI or VI'' was formed. The reaction mixture was cooled to 0° C. and imidazoquinoline VII or oxoadenine VIII (1.0 eq) and imidazolium triflate (1.5 eq) were added. The reaction mixture was allowed to warm up to rt. The reaction was usually completed after 1 hour at rt.

The resulting phosphite IX", IX*  or IX*" can be purified at this stage or subsequently oxidized without isolation.

Example 2: General Procedure for the Oxidation of IX

The phosphotriester IX, IX", IX* or IX*" (purified or not) in a solution of methylene chloride was oxidized by addition of t-butyl hydroperoxide (1.5 eq) to the reaction mixture and stirring at rt for 30 min. After completion of the oxidation, the reaction mixture was concentrated under vacuum and purified by chromatography on silica gel. The resulting protected phosphotriester was dissolved in acetonitrile (0.06 M). Triethylamine (acetonitrile:TEA 1:0.35 v:v) was added and the reaction mixture stirred at rt for 6 to 18 hours. Once the deprotection was complete, the reaction mixture was filtered over a Büchner filter and the isolated solid rinsed with acetonitrile and dried under high vacuum. The reaction mixture can also be purified by chromatography on silica gel.

Example 3: Synthesis of 4-amino-1-[2-(1,2-di-O-palmitoyl-sn-glycero-3-phospho)ethyl]-2-n-butyl-1H-imidazo[4,5-c]quinoline, Compound (Ia)

$R_1$=n-Bu, Z=$(CH_2)_2$, n=0, $R_2$=$R_3$=n-$C_{15}H_{31}$CO

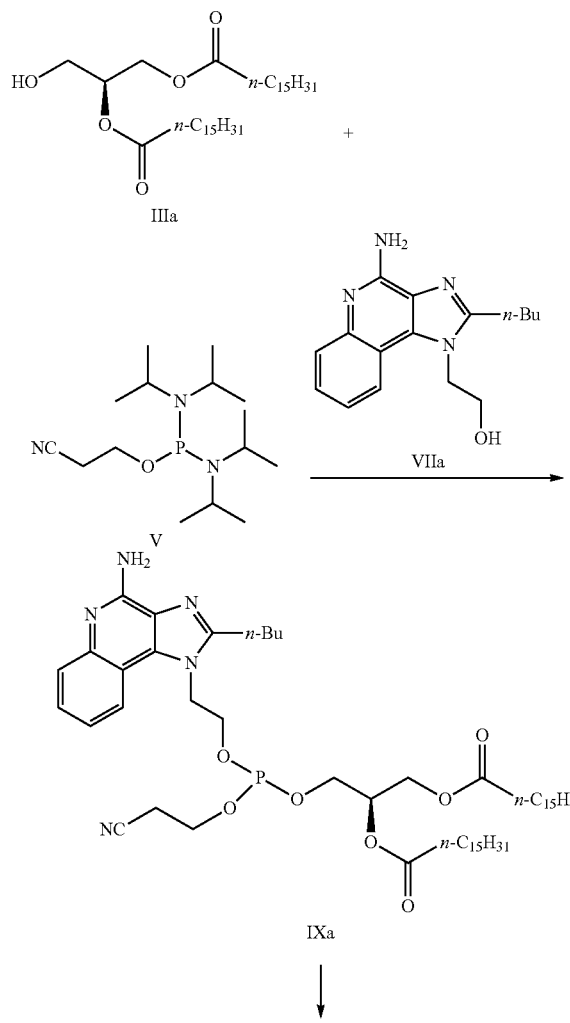

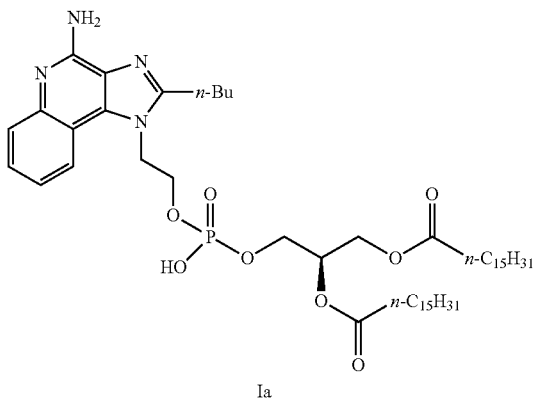

Phosphotriester IXa was prepared in 93% yield by reacting di-O-palmitoyl glycerol IIIa with V followed by addition of imidazoquinoline VIIa and imidazolium triflate as described in example 1. IXa was oxidized and deprotected following the procedure described in example 2 to give phospholipidated imidazoquinoline Ia in 71% yield.

$^1$H NMR (CDCl$_3$/CD$_3$OD, 400 MHz): δ 8.23 (bs, 1H), 7.39 (t, 1H), 7.22 (bs, 1H), 6.93 (bs, 1H), 5.25 (m, 1H), 4.70 (bs, 2H), 4.60 (bs, 2H), 4.42 (dd, 1H), 4.19 (dd, 1H), 4.04 (t, 2H), 3.06 (bs, 2H), 2.32 (m, 4H), 1.96 (m, 2H), 1.59 (m, 6H), 1.26 (m, 48H), 1.07 (t, 3H), 0.88 (m, 6H); Positive ES TOF-MS calcd for [M+H]$^+$ 915.6340; found 915.6309.

Example 4: Synthesis of 4-amino-1-[2-(1,2-di-O-palmitoyl-sn-glycero-3-phospho)ethyl]-2-ethoxymethyl-1H-imidazo[4,5-c]quinoline, Compound (Ib)

$R_1$=CH$_2$OEt, Z=$(CH_2)_2$, n=0, $R_2$=$R_3$=n-$C_{15}H_{31}$CO

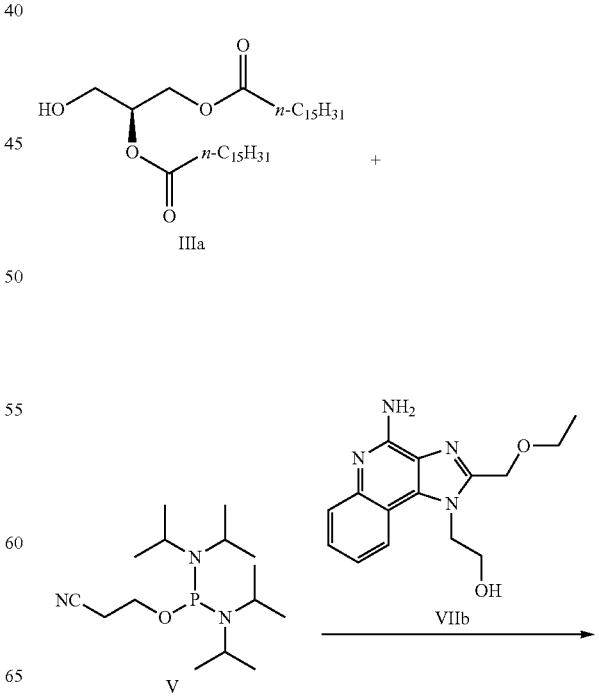

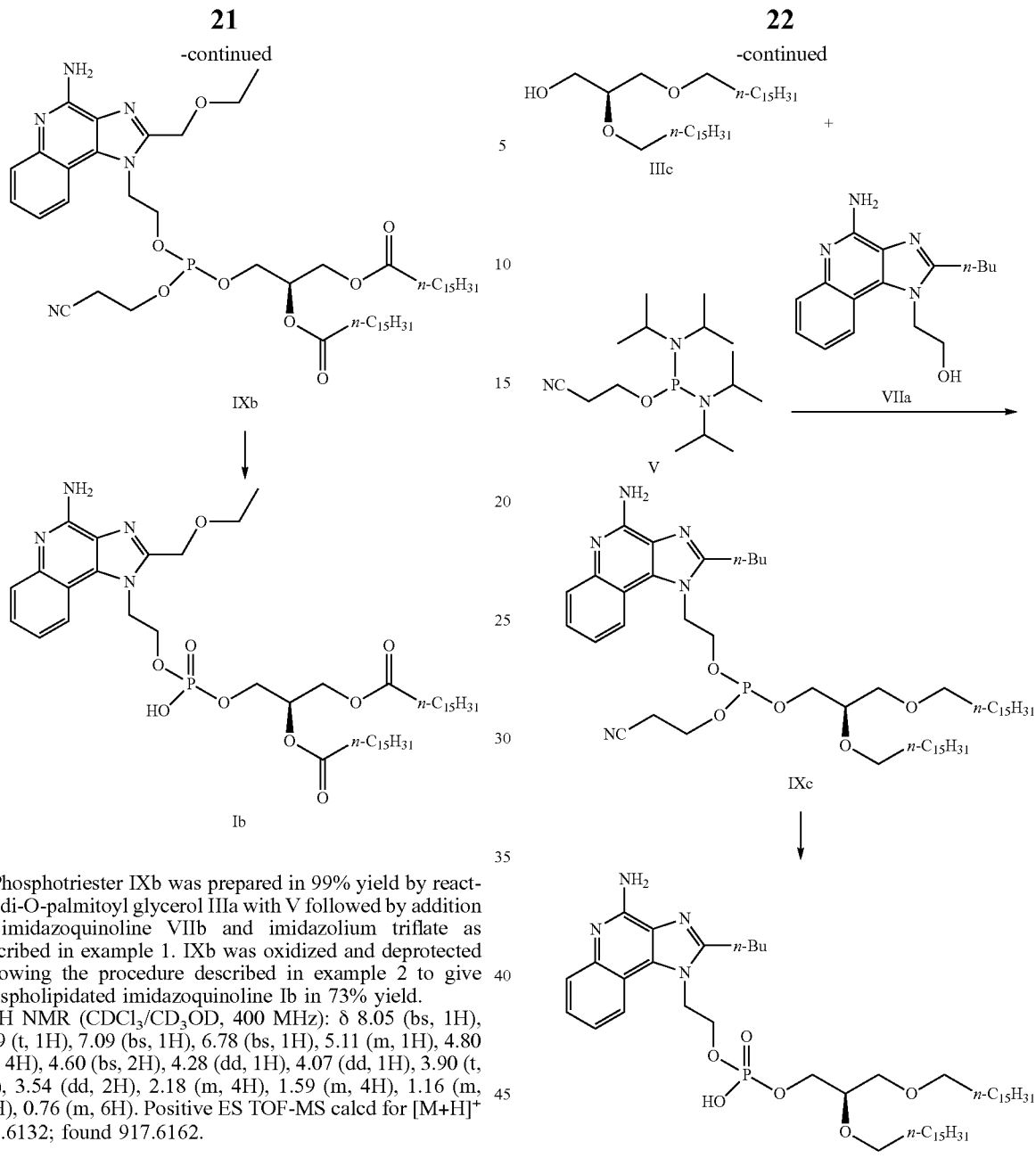

Phosphotriester IXb was prepared in 99% yield by reacting di-O-palmitoyl glycerol IIIa with V followed by addition of imidazoquinoline VIIb and imidazolium triflate as described in example 1. IXb was oxidized and deprotected following the procedure described in example 2 to give phospholipidated imidazoquinoline Ib in 73% yield.

$^1$H NMR (CDCl$_3$/CD$_3$OD, 400 MHz): δ 8.05 (bs, 1H), 7.29 (t, 1H), 7.09 (bs, 1H), 6.78 (bs, 1H), 5.11 (m, 1H), 4.80 (bs, 4H), 4.60 (bs, 2H), 4.28 (dd, 1H), 4.07 (dd, 1H), 3.90 (t, 2H), 3.54 (dd, 2H), 2.18 (m, 4H), 1.59 (m, 4H), 1.16 (m, 51H), 0.76 (m, 6H). Positive ES TOF-MS calcd for [M+H]$^+$ 917.6132; found 917.6162.

Example 5: Synthesis of 4-amino-1-[2-(1,2-di-O-hexadecyl-sn-glycero-3-phospho)ethyl]-2-n-butyl-1H-imidazo[4,5-c]quinoline, Compound (Ic)

R$_1$=n-Bu, Z=(CH$_2$)$_2$, n=0, R$_2$=R$_3$=n-C$_{15}$H$_{31}$

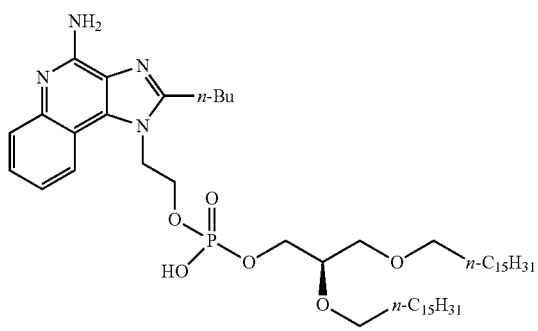

Phosphotriester IXc was prepared in 97% yield by reacting di-O-hexadecyl glycerol IIIc with V followed by addition of imidazoquinoline VIIa and imidazolium triflate as described in example 1. IXc was oxidized and deprotected following the procedure described in example 2 to give phospholipidated imidazoquinoline Ic in 71% yield.

$^1$H NMR (CDCl$_3$/CD$_3$OD, 400 MHz): δ 8.23 (bs, 1H), 7.40 (t, 1H), 7.18 (bs, 1H), 6.96 (bs, 1H), 4.70 (bs, 2H), 4.60 (bs, 2H), 3.95 (t, 2H), 3.50 (mm, 7H), 4.04 (t, 2H), 3.03 (bs, 2H), 1.94 (m 2H), 1.56 (m, 6H), 1.26 (m, 52H), 1.06 (t, 3H), 0.88 (t, 6H). Positive ES TOF-MS calcd for [M+H]$^+$ 885.6598. found 885.8304.

Example 6: Synthesis of 4-amino-1-[2-(1,2-di-O-lauroyl-sn-glycero-3-phospho)ethyl]-2-n-butyl-1H-imidazo[4,5-c]quinoline, Compound (Id)

R1=n-Bu, Z=(CH$_2$)$_2$, n=0, R$_2$=R$_3$=n-C$_{11}$H$_{23}$CO

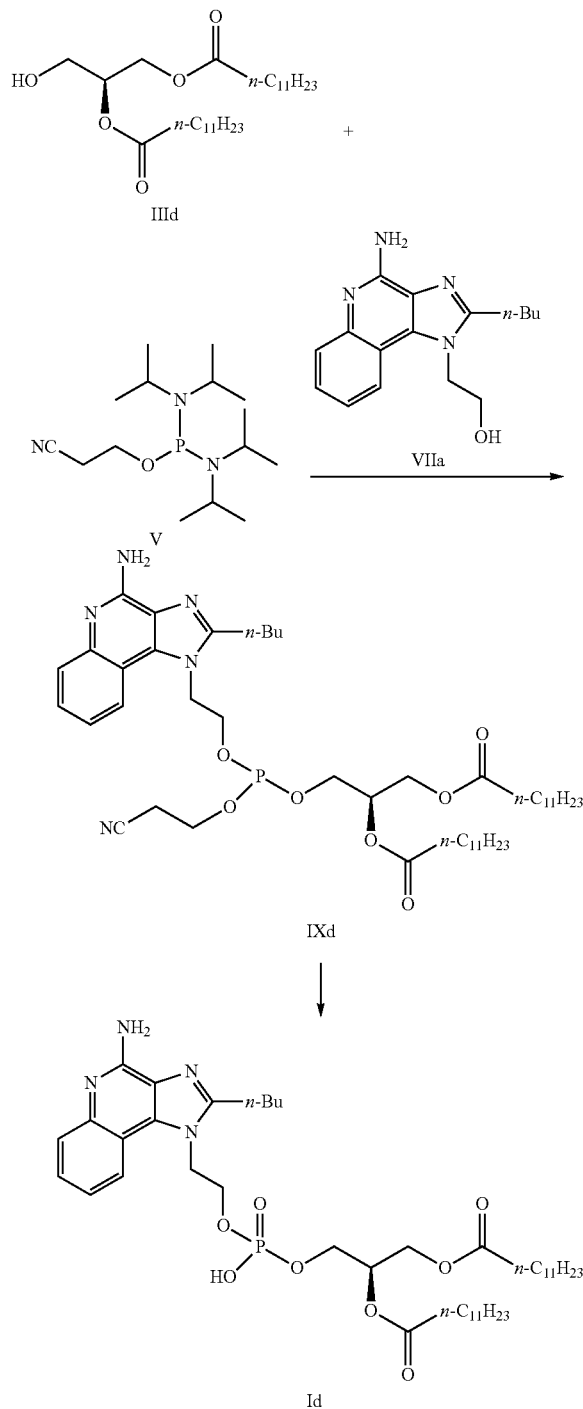

Phosphotriester IXd was prepared in 79% yield by reacting di-O-lauroyl glycerol IIId with V followed by addition of imidazoquinoline VIIa and imidazolium triflate as described in example 1. IXd was oxidized and deprotected following the procedure described in example 2 to give phospholipidated imidazoquinoline Id in 77% yield.

$^1$H NMR (CDCl$_3$/CD$_3$OD, 400 MHz): δ 8.09 (bs, 1H), 7.30 (t, 1H), 7.09 (bs, 1H), 6.81 (bs, 1H), 5.12-5.17 (m, 1H), 4.22-4.76 (m, 4H), 4.31 (dd, 1H), 4.11 (dd, 1H), 3.93 (t, 2H, 1H), 2.93 (bs, 2H), 2.20 (dd, 4H), 1.84 (m, 2H), 1.42-1.49 (m, 6H), 1.15 (m, 34H), 0.96 (t, 3H), 0.78 (t, 6H). Negative ES TOF-MS calc for [M–H]$^-$ 801.4931; found 801.4741.

Example 7: Synthesis of 4-amino-1-[2-(1,2-di-O-myristoyl-sn-glycero-3-phospho)ethyl]-2-n-butyl-1H-imidazo[4,5-c]quinoline, Compound (Ie)

R1=n-Bu, Z=(CH$_2$)$_2$, n=0, R$_2$=R$_3$=n-C$_{13}$H$_{27}$CO

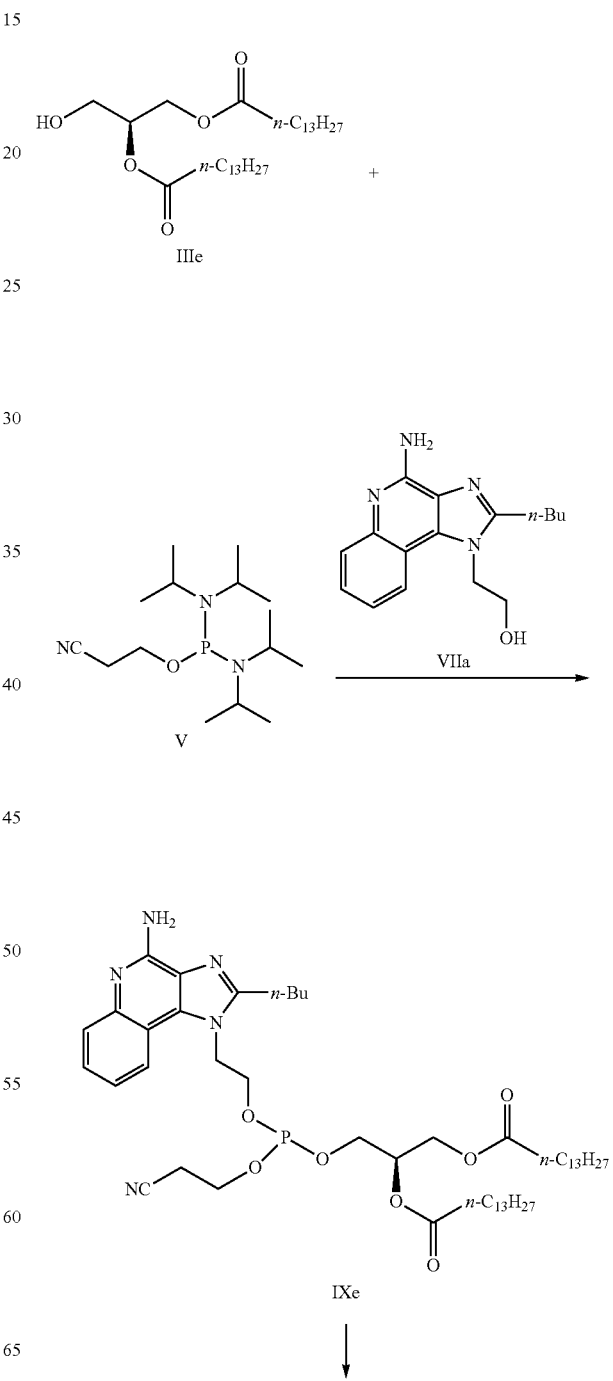

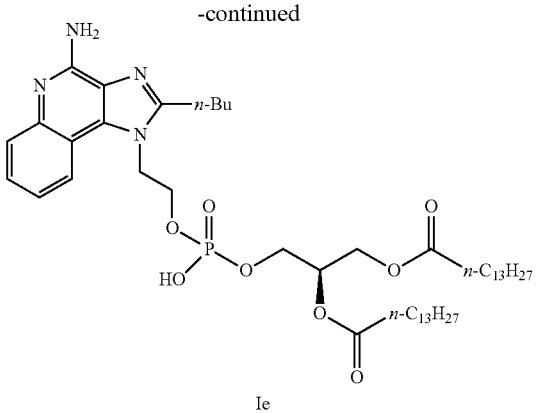

Ie

Phosphotriester IXe was prepared in 62% yield by reacting di-O-myristoyl glycerol IIIe with V followed by addition of imidazoquinoline VIIa and imidazolium triflate as described in example 1. IXe was oxidized and deprotected following the procedure described in example 2 to give phospholipidated imidazoquinoline Ie in 89% yield.

$^1$H NMR (CDCl$_3$/CD$_3$OD, 400 MHz): δ 8.17 (bs, 1H), 7.39 (bs, 1H), 7.17 (bs, 1H), 6.91 (bs, 1H), 5.24 (m, 1H), 4.80 (bs, 2H), 4.60 (bs, 2H), 4.41 (dd, 1H), 4.19 (dd, 1H), 4.03 (t, 2H), 2.99 (bs, 2H), 2.30 (m, 4H), 1.94 (bs, 2H), 1.57 (m, 6H), 1.25 (m, 40H), 1.05 (t, 3H), 0.88 (m, 6H). Positive ES TOF-MS calcd for [M+H]$^+$ 857.5558; found 857.5565.

Example 8: Synthesis of 4-amino-1-[2-(1,2-di-O-oleoyl-sn-glycero-3-phospho)ethyl]-2-n-butyl-1H-imidazo[4,5-c]quinoline, Compound (If)

R1=n-Bu, Z=(CH$_2$)$_2$, n=0, R$_2$=R$_3$=(CH$_2$)$_7$CH=CH(CH$_2$)$_7$CH$_3$

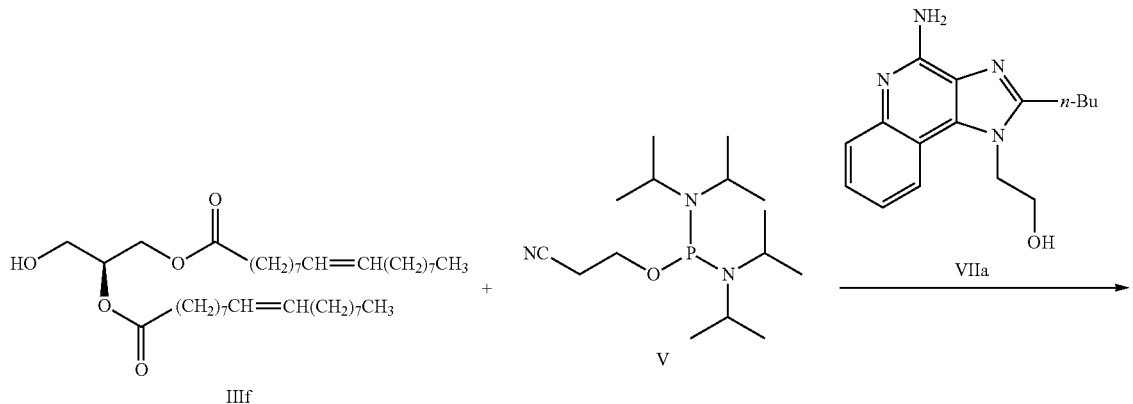

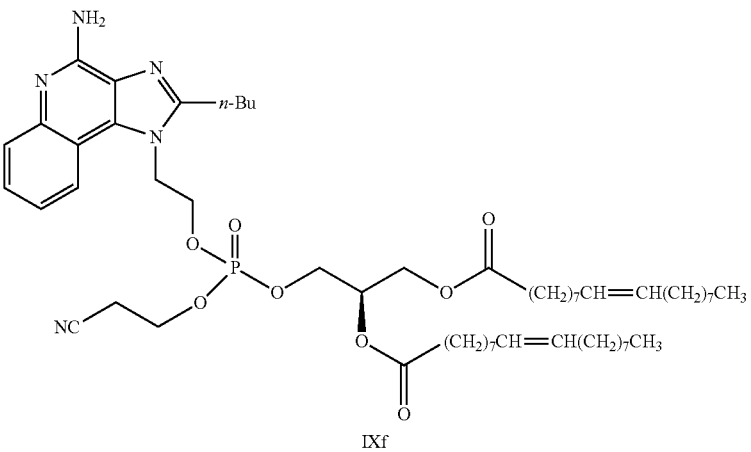

IXf

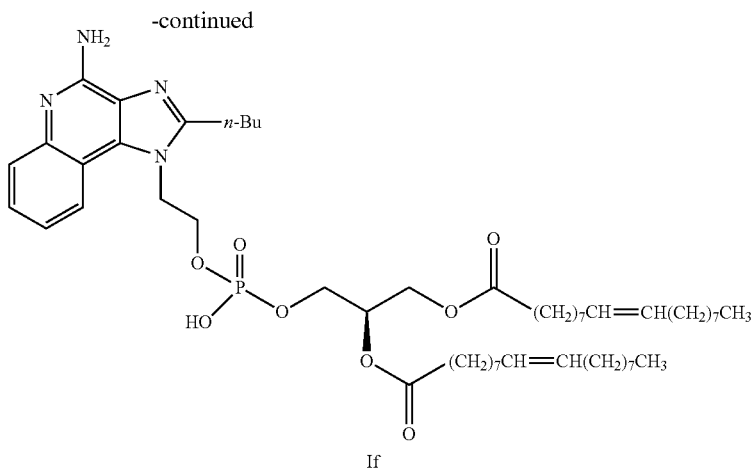

If

Phosphotriester IXf was prepared in 92% yield by reacting di-O-oleoyl glycerol IIIf with V followed by addition of imidazoquinoline VIIa and imidazolium triflate as described in example 1. IXf was oxidized and deprotected following the procedure described in example 2 to give phospholipidated imidazoquinoline If in 75% yield.

$^1$H NMR (400 MHz, CDCl$_3$/CD$_3$OD) δ 8.18 (bs, 1H), 7.39 (bs, 1H), 7.18 (bs, 1H), 6.92 (bs, 1H), 5.33 (m, 4H), 5.25 (m, 1H), 4.80 (bs, 2H), 4.60 (bs, 2H), 4.41 (dd, J=3.2, 12.0 Hz, 1H), 4.19 (dd, J=6.4, 12.0 Hz, 1H), 4.03 (t, J=6.0 Hz, 2H), 3.01 (bs, 2H), 2.30 (m, 4H), 1.98 (m, 4H), 1.57 (m, 6H), 1.27 (m, 40H), 1.05 (t, J=7.2, 3H), 0.88 (m, 6H); negative ES TOF-MS calc for [M−H]$^−$ 965.6497, found 965.6498.

Example 9: Synthesis of 4-amino-1-[2-O-(ethylcholestero-3-phospho)ethyl]-2-n-butyl-1H-imidazo[4.5-c]quinoline, Compound (Ig)

R$_1$=n-Bu, Z=(CH$_2$)$_2$, n=1

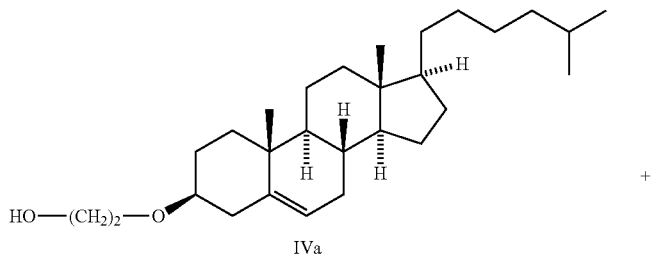

IVa

+

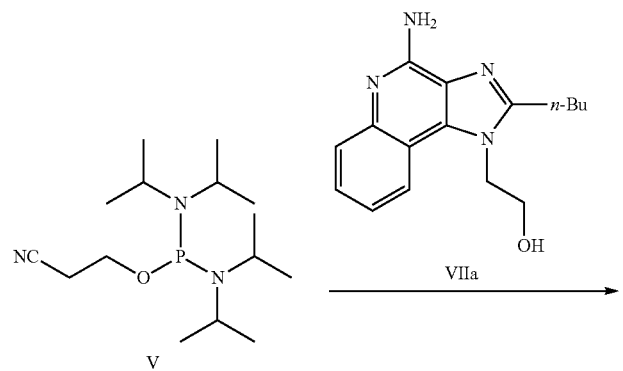

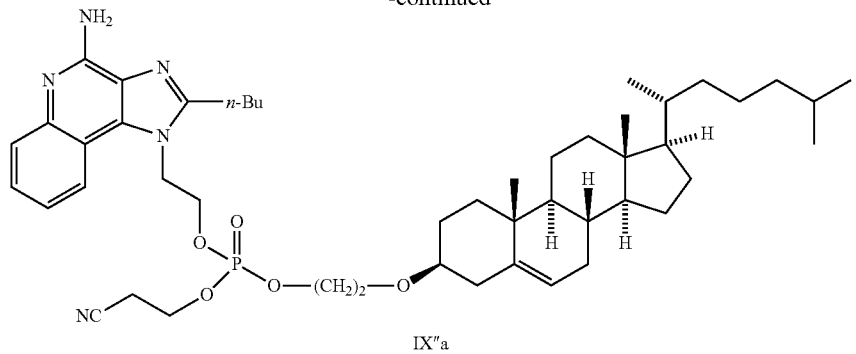

IX''a

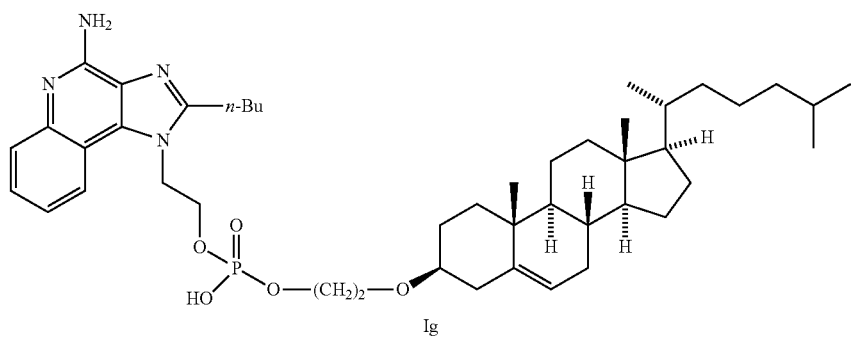

Ig

Phosphotriester IX''a was prepared in 99% yield by reacting ethyl cholesterol IVa with V followed by addition of imidazoquinoline VIIa and imidazolium triflate as described in example 1. IX''a was oxidized and deprotected following the procedure described in example 2 to give phospholipidated imidazoquinoline Ig in 44% yield.

$^1$H NMR (400 MHz, CDCl$_3$/CD$_3$OD) δ 10.17 (bs, 1H), 9.90 (bs, 0.5H), 8.40 (bs, 0.5H), 8.08 (d, 1H), 7.45 (bs, 1H), 7.29 (t, 1H), 7.02 (t, 1H), 6.86 (d, 1H), 6.11 (bs, 1H), 5.30 (bs, 2H), 4.95-4.40 (m, 4H), 4.02 (d, 2H), 3.68 (t, 2H), 3.3-2.8 (m, 3H), 2.36 (d, 1H), 2.18 (t, 1H), 2.0-1.8 (m, 8H), 1.4-0.8 (m, 39H), 0.68 (s, 3H). Positive ES TOF-MS calc for [M+H]$^+$ 777.5084; found 777.6999.

Example 10: Synthesis of 4-amino-1-[2-O-(butylcholestero-3-phospho)ethyl]-2-n-butyl-1H-imidazo[4.5-c]quinoline, Compound (Ih)

R$_1$=n-Bu, Z=(CH$_2$)$_2$, n=1

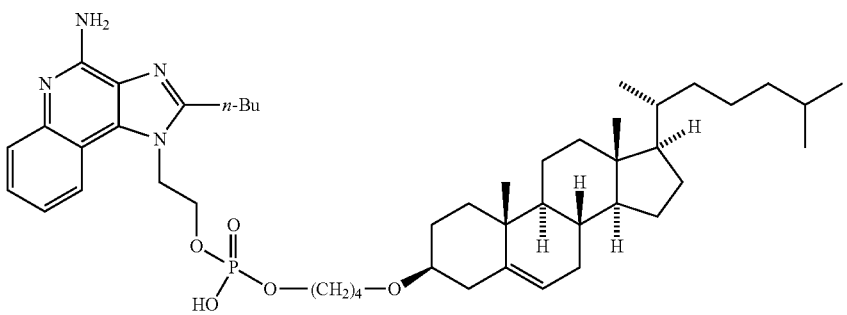

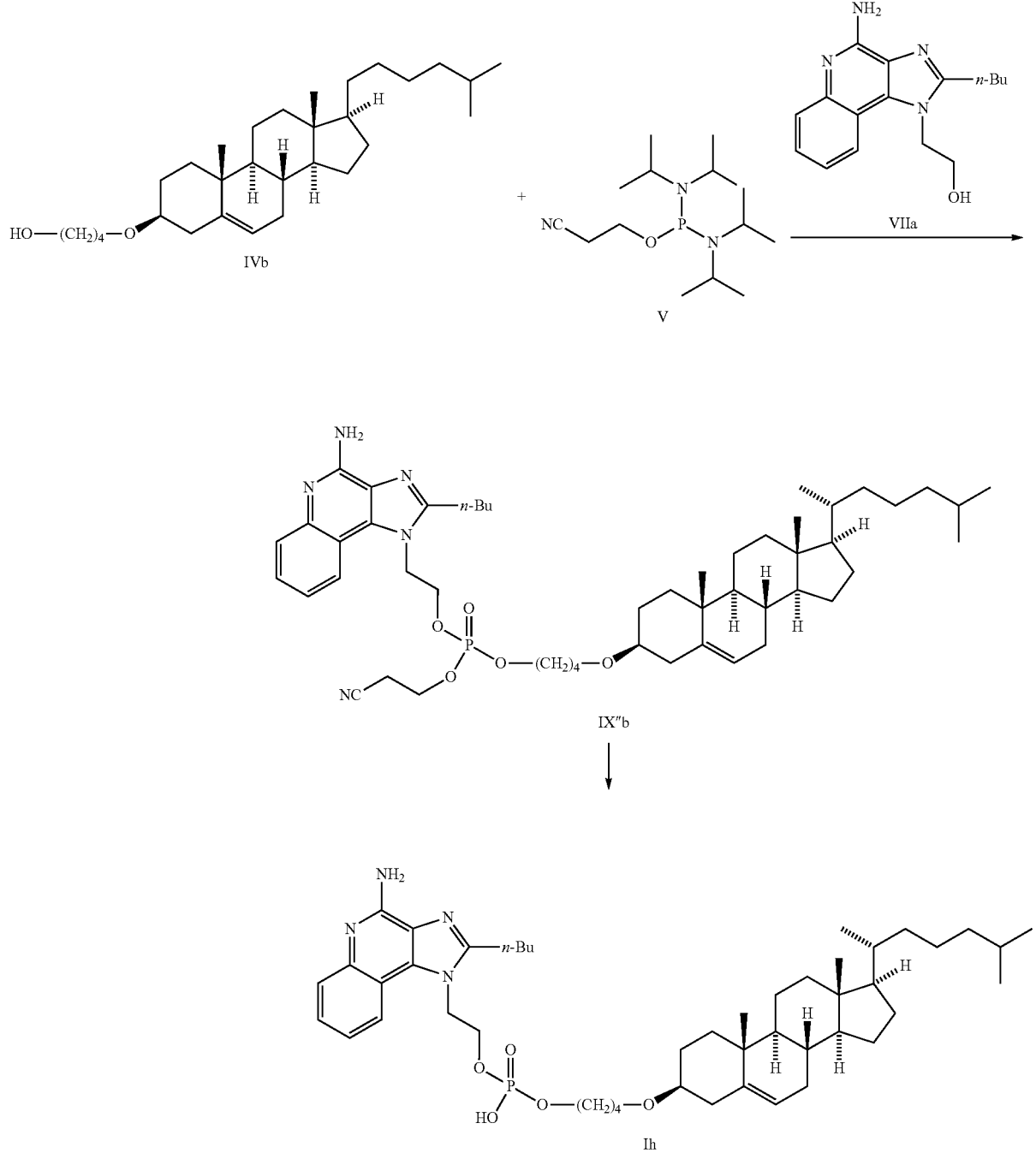

Phosphotriester IX″b was prepared in 96% yield by reacting butyl cholesterol IVb with V followed by addition of imidazoquinoline VIIa and imidazolium triflate as described in example 1. IX″b was oxidized and deprotected following the procedure described in example 2 to give phospholipidated imidazoquinoline Ih in 56% yield.

$^1$H NMR (400 MHz, CDCl$_3$/CD$_3$OD) δ 8.01 (bs, 1H), 7.31 (bs, 1H), 7.04 (bs, 1H), 6.88 (bs, 1H), 5.32 (m, 2H), 4.82 (bs, 2H), 4.53 (bs, 2H), 3.92 (m, 2H), 3.48 (m, 2H), 3.2-2.8 (m, 2H), 2.32 (m, 1H), 2.16 (m, 1H), 1.62-2.10 (m, 11H), 0.97-1.60 (2m, 9H), 0.86-0.95 (m, 9H), 0.68 (s, 3H); negative ES TOF-MS calc for [M−H]$^-$ 803.5240, found 803.5923.

Example 11: Synthesis of 6-amino-2-butoxy-9-[N-(2-(1,2-di-O-palmitoyl-sn-glycero-3-phosphoramido)ethy)-4-piperidinylmethyl]-8-hydroxypurine, Compound (IIa)

R=n-butoxy, d=1, X=CH, Y=N, m=2, n=0, R=R$_3$=n-C$_{15}$H$_{31}$CO

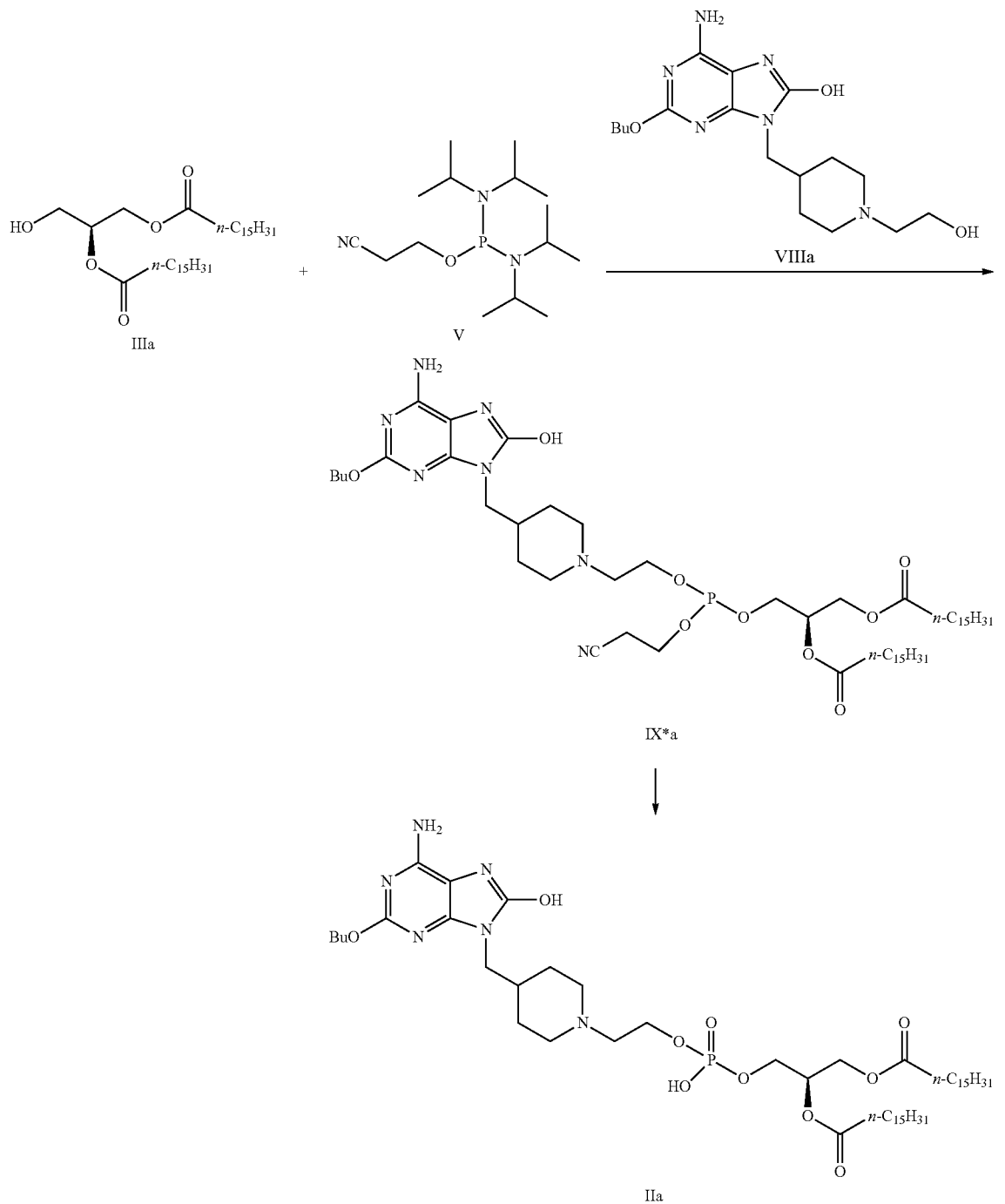

Phosphotriester IX*a was prepared in 33% yield by reacting di-O-palmitoyl glycerol IIIa with V followed by addition of oxoadenine VIIIa and imidazolium triflate as described in example 1. IX*a was oxidized and deprotected following the procedure described in example 2 to give phospholipidated oxoadenine IIa in 56% yield.

$^1$H NMR (CDCl$_3$/CD$_3$OD, 400 MHz): δ 5.17 (bs, 1H), 4.32 (dd, 1H), 4.20-4.09 (m, 5H), 3.98 (br t, 2H), 3.69 (br d, 3H), 3.23 (br s, 1H), 1.86 (br s, 4H), 1.69 (m, 2H), 1.53 (br s, 4H), 1.42 (dd, 2H), 1.20 (m, 48H), 0.91 (t, 3H), 0.83 (t, 6H). Negative ES TOF-MS calc for [M−H]$^-$ 993.6768; found 993.6782.

Example 12: Synthesis of 6-amino-2-butoxy-9-[N-(2-(1,2-di-O-oleoyl-sn-glycero-3-phosphoramido) ethyl)-4-piperidinylmethyl]-8-hydroxypurine, Compound (IIb)

R=n-butoxy, d=1, X=CH, Y=N, m=2, n=0, R$_2$=R$_3$= (CH$_2$)$_7$CH=CH(CH$_2$)$_7$CH$_3$

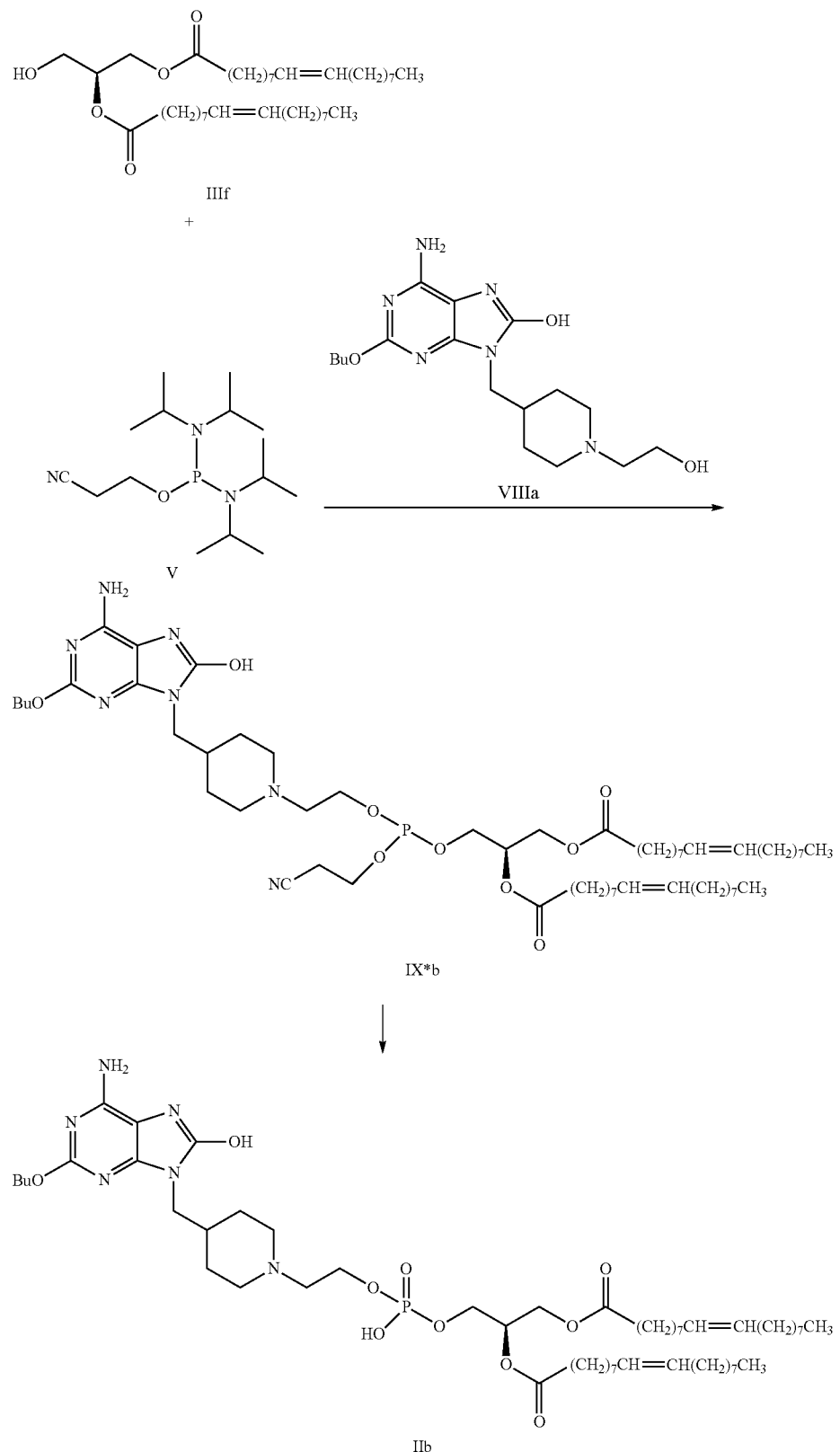
Phosphotriester IX*b was prepared in 58% yield by reacting di-O-oeloyl glycerol IIIf with V followed by addition of oxoadenine VIIIa and imidazolium triflate as described in example 1. IX*b was oxidized and deprotected following the procedure described in example 2 to give phospholipidated oxoadenine IIb in 73% yield.

$^1$H NMR (CDCl$_3$/CD$_3$OD, 400 MHz): δ 5.3 (m, 4H), 5.23 (m, 1H), 4.37 (dd, 1H), 4.20 (m, 5H), 4.04 (t, 2H), 3.70 (m, 4H), 3.27 (bs, 2H), 2.74 (m, 2H), 2.30 (m, 5H), 2.00 (m, 12H), 1.75 (m, 2H), 1.60 (bs, 4H), 1.48 (m, 2H), 1.30 (m, 40H), 0.97 (t, 3H), 0.88 (t, 3H). Negative ES TOF-MS calc for [M−H]⁻ 1045.7082; found 1045.2163.

The invention claimed is:

1. A process for preparing a compound of formula (I) comprising the steps of:

a) reacting a compound of formula (IV)

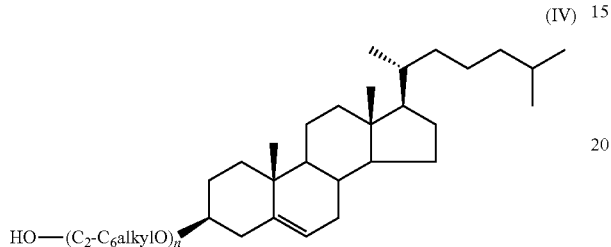

(IV)

wherein
n is 0, 1, 2, 3, 4, 5, 6, 7, 8, 9, 10, 11, 12, 13, 14, 15, 16, 17, 18, 19, or 20;
with a compound of formula (V)

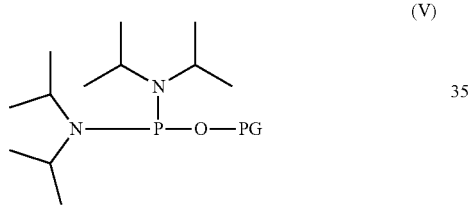

(V)

wherein
PG is a protecting group suitable for hydroxyl protection, including but not limited to cyanoethyl, methyl, ethyl, benzyl and allyl group;
to prepare a compound of formula (VI)'';

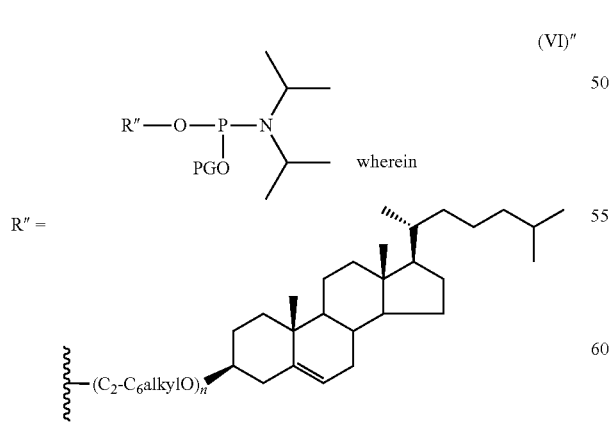

(VI)''

PG is a protecting group suitable for hydroxyl protection, including but not limited to cyanoethyl, methyl, ethyl, benzyl and allyl group; and n is 0, 1, 2, 3, 4, 5, 6, 7, 8, 9, 10, 11, 12, 13, 14, 15, 16, 17, 18, 19, or 20;

b) reacting a compound of formula (VI)'' with a compound of formula (VII)

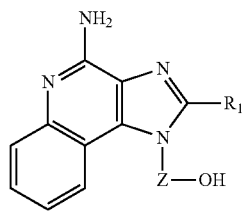

(VII)

wherein
R$_1$ is selected from H, C$_{1-6}$alkyl, C$_{1-6}$alkylamino, C$_{1-6}$alkoxy, C$_{3-6}$cycloalkylC$_{1-6}$alkyl, C$_{3-6}$cycloalkylC$_{1-6}$alkylamino, C$_{3-6}$cycloalkylC$_{1-6}$alkoxy, C$_{1-6}$alkoxyC$_{1-6}$alkyl, C$_{1-6}$alkoxyC$_{1-6}$alkylamino and C$_{1-6}$alkoxyC$_{1-6}$alkoxy; wherein the C$_{1-6}$alkyl, C$_{1-6}$alkylamino, C$_{1-6}$alkoxy, C$_{3-6}$cycloalkylC$_{1-6}$alkyl, C$_{3-6}$cycloalkylC$_{1-6}$alkylamino, C$_{3-6}$cycloalkylC$_{1-6}$alkoxy, C$_{1-6}$alkoxyC$_{1-6}$alkyl, C$_{1-6}$alkoxyC$_{1-6}$alkylamino or C$_{1-6}$alkoxyC$_{1-6}$alkoxy is branched or unbranched and optionally terminally substituted with a hydroxyl, amino, thio, hydrazino, hydrazido, azido, acetylenyl, carboxyl, or maleimido group;
Z is selected from C$_2$-C$_6$ alkyl and C$_2$-C$_6$ alkenyl, wherein the C$_2$-C$_6$ alkyl or C$_2$-C$_6$ alkenyl is unsubstituted or terminally substituted by —(O—C$_2$-C$_6$alkyl)$_{1-6}$—;
to prepare a compound of formula (IX)''; and

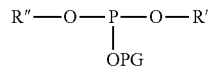

(IX)'' wherein

R'' =

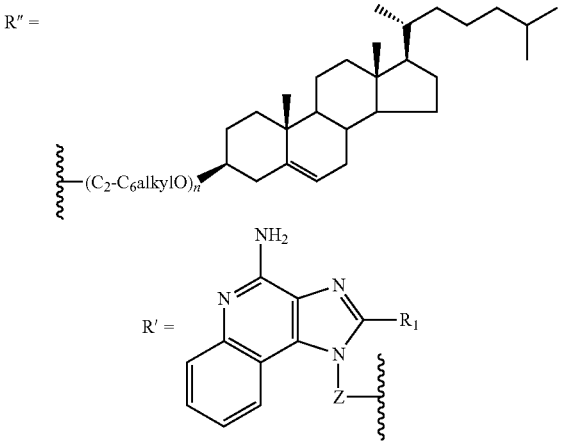

c) oxidizing a compound of formula (IX)'' and removing the hydroxyl protecting group to obtain a compound of formula (I)

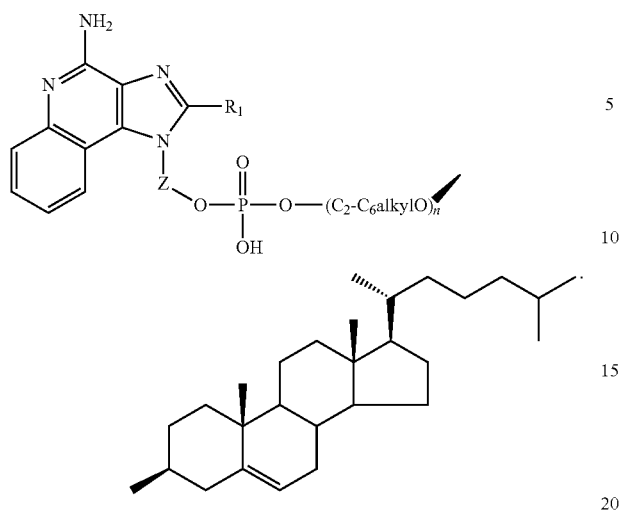

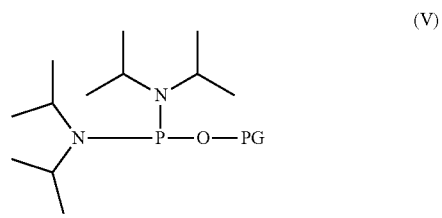

wherein
PG is a protecting group suitable for hydroxyl protection, including but not limited to cyanoethyl, methyl, ethyl, benzyl and allyl group;
to prepare a compound of formula (VI); and

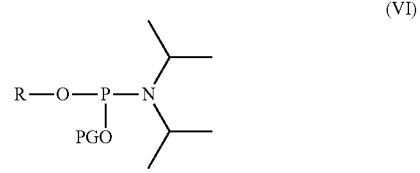

wherein
R is

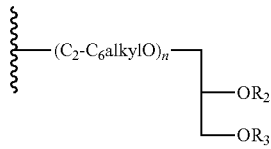

b) reacting a compound of formula (VI) with a compound of formula (VIII)

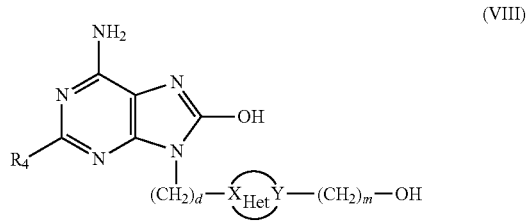

wherein
d is 0, 1, 2, 3, 4, 5 or 6;
Het is a four-, five-, or six membered saturated nitrogen heterocycle wherein X,Y=CH or N, and at least one of X and Y is a nitrogen atom;
m is 0, 1, 2, 3, 4, 5 or 6;
to prepare a compound of formula (IX)*; and

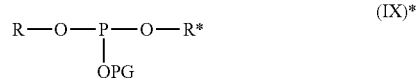

2. The process of claim 1 wherein 1H-tetrazole is added to a compound of formula (IV).

3. The process of claim 1 wherein 1H-tetrazole is added in several portions over 20 to 40 minutes.

4. The process of claim 1 wherein imidazolium triflate is added with a compound of formula (VII).

5. The process of claim 1 wherein the coupling agent used with a compound of formula (IV) and a compound of formula (V) is at 2.1 equivalents, the compound of formula (IV) is at 2.0 equivalents, the compound of formula (V) is at 2.1 equivalents, the compound of formula (VII) is at 1.0 equivalent and the oxidizing agent for the compound of formula (IX)" is at 1.5 equivalent.

6. The process of claim 4 wherein imidazolium triflate is added with the compound of formula (VII) to the same reaction mixture produced by the reaction of compound of formula (V) with the compound of formula (IV).

7. The process of claim 1 wherein the reaction mixture containing the compound of formula (VI)" is cooled to 0° C. before the addition of a compound of formula (VII).

8. The process of claim 1 wherein the hydroxyl protecting group is cyanoethyl and deprotection is with triethylamine (TEA).

9. A process for preparing a compound of formula (II) comprising the steps of:
a) reacting a compound of formula (III)

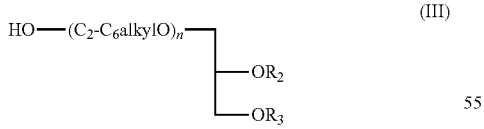

wherein
n is 0, 1, 2, 3, 4, 5, 6, 7, 8, 9, 10, 11, 12, 13, 14, 15, 16, 17, 18, 19, or 20;
$R_2$ is H or a straight or branched, optionally unsaturated, $C_4$-$C_{24}$ alkyl, or a straight or branched, optionally unsaturated, $C_4$-$C_{24}$ acyl;
$R_3$ is a straight or branched, optionally unsaturated, $C_4$-$C_{24}$ alkyl or a straight or branched, optionally unsaturated, $C_4$-$C_{24}$ acyl;

with a compound of formula (V)

wherein
R is

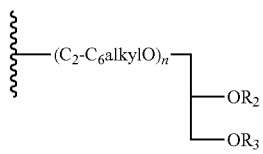

R* is

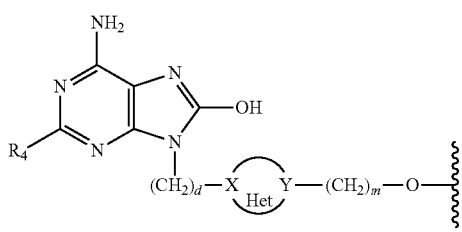

c) oxidizing a compound of formula (IX)* and removing the hydroxyl protecting group to obtain a compound of formula (II)

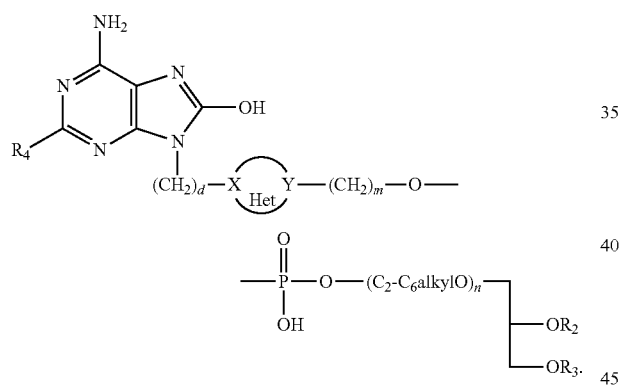

10. A process for preparing a compound of formula (II) comprising the steps of:

a) reacting a compound of formula (IV)

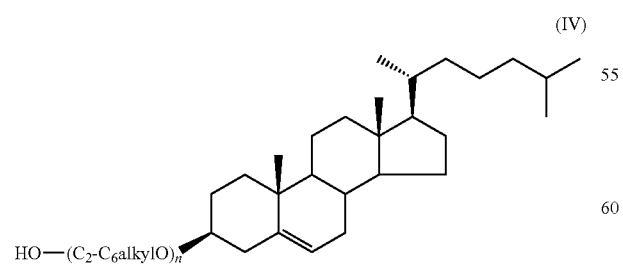

wherein
n is 0, 1, 2, 3, 4, 5, 6, 7, 8, 9, 10, 11, 12, 13, 14, 15, 16, 17, 18, 19, or 20;

with a compound of formula (V)

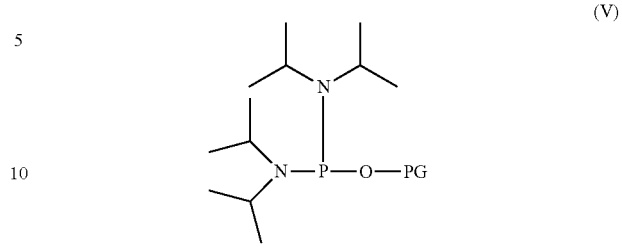

wherein
PG is a protecting group suitable for hydroxyl protection, including but not limited to cyanoethyl, methyl, ethyl, benzyl and allyl group;
to prepare a compound of formula (VI)'';

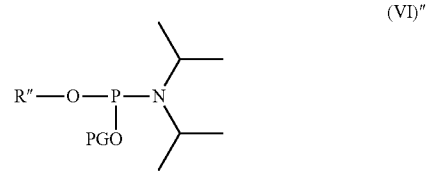

wherein
R'' is

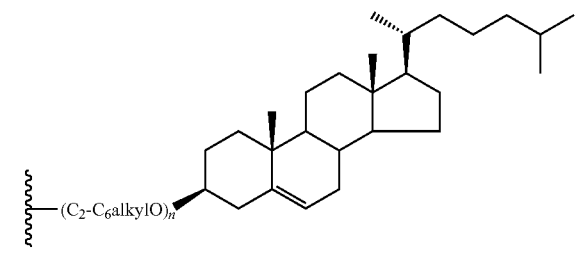

b) reacting a compound of formula (VI)'' with a compound of formula (VIII)

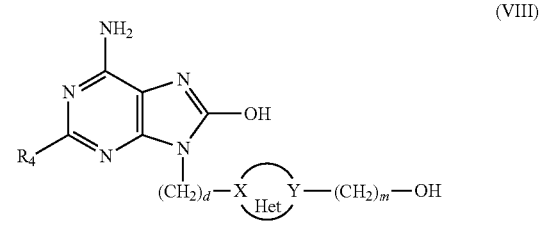

wherein
d is 0, 1, 2, 3, 4, 5 or 6;
Het is a four-, five-, or six membered saturated nitrogen heterocycle wherein X,Y=CH or N, and at least one of X and Y is a nitrogen atom;
m is 0, 1, 2, 3, 4, 5 or 6;
to prepare a compound of formula (IX)*'';

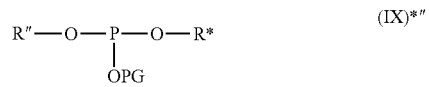

wherein
R" is

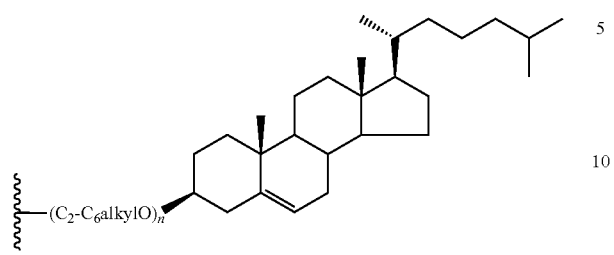

R* is

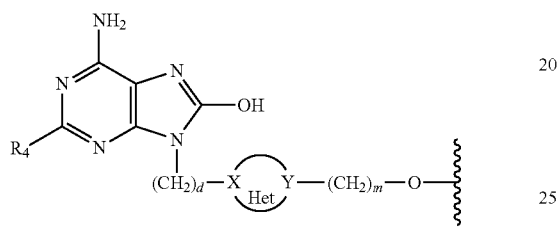

c) oxidizing a compound of formula (IX)*" and removing the hydroxyl protecting group to obtain a compound of formula (II)

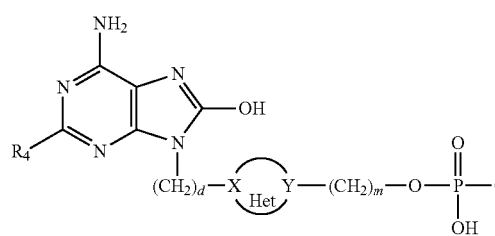

11. A process of preparing a compound of formula (I) comprising the steps of:

a) reacting a compound of formula (III)

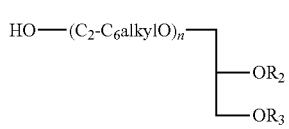

wherein n is 0;

$R_2$ is H or a straight or branched, optionally unsaturated, $C_4$-$C_{24}$ alkyl, or a straight or branched, optionally unsaturated, $C_4$-$C_{24}$ acyl;

$R_3$ is a straight or branched, optionally unsaturated, $C_4$-$C_{24}$ alkyl or a straight or branched, optionally unsaturated, $C_4$-$C_{24}$ acyl;

with a compound of formula (V)

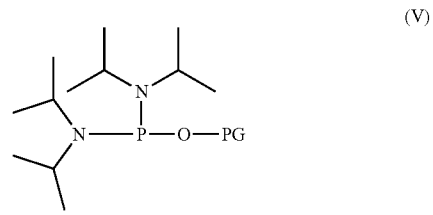

wherein

PG is a protecting group suitable for hydroxyl protection, including but not limited to cyanoethyl, methyl, ethyl, benzyl and allyl group;

to prepare a compound of formula (VI);

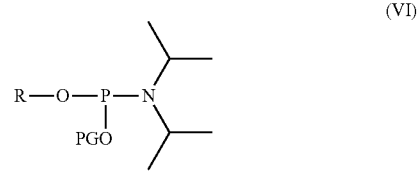

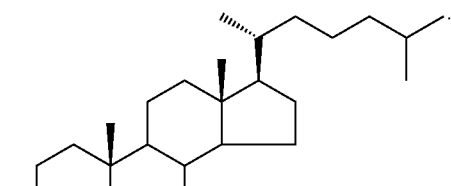

wherein

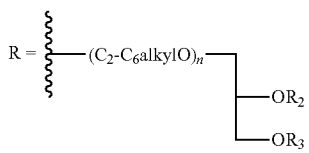

b) reacting a compound of formula (VI) with a compound of formula (VII)

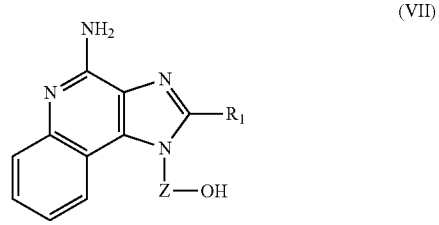

wherein

R₁ is selected from H, $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino and $C_{1-6}$alkoxy$C_{1-6}$alkoxy; wherein the $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino or $C_{1-6}$alkoxy$C_{1-6}$alkoxy is branched or unbranched and optionally terminally substituted with a hydroxyl, amino, thio, hydrazino, hydrazido, azido, acetylenyl, carboxyl, or maleimido group;

Z is selected from $C_2$-$C_6$ alkyl and $C_2$-$C_6$ alkenyl, wherein the $C_2$-$C_6$ alkyl or $C_2$-$C_6$ alkenyl is unsubstituted or terminally substituted by —(O—$C_2$-$C_6$alkyl)$_{1-6}$—;

to prepare a compound of formula (IX); and

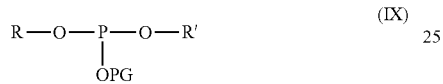

(IX)

wherein

PG is a protecting group suitable for hydroxyl protection, including but not limited to cyanoethyl, methyl, ethyl, benzyl and allyl group;

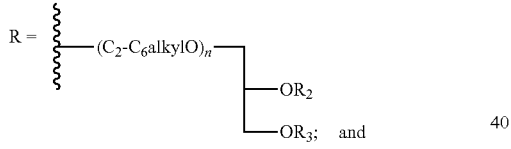

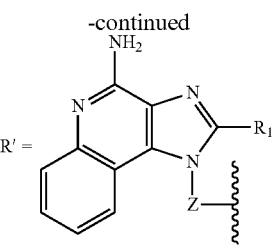

wherein

R₁ is selected from H, $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino and $C_{1-6}$alkoxy$C_{1-6}$alkoxy; wherein the $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino or $C_{1-6}$alkoxy$C_{1-6}$alkoxy is branched or unbranched and optionally terminally substituted with a hydroxyl, amino, thio, hydrazino, hydrazido, azido, acetylenyl, carboxyl, or maleimido group;

Z is selected from $C_2$-$C_6$ alkyl and $C_2$-$C_6$ alkenyl, wherein the $C_2$-$C_6$ alkyl or $C_2$-$C_6$ alkenyl is unsubstituted or terminally substituted by —(O—$C_2$-$C_6$alkyl)$_{1-6}$—;

c) oxidizing a compound of formula (IX) and removing the hydroxyl protecting group to obtain a compound of formula (I)

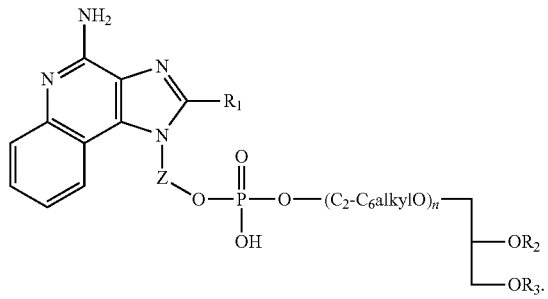

* * * * *